(12) United States Patent
Renold et al.

(10) Patent No.: US 9,493,445 B2
(45) Date of Patent: *Nov. 15, 2016

(54) INSECTICIDAL COMPOUNDS

(71) Applicants: Syngenta Crop Protection LLC, Greensboro, NC (US); Syngenta Limited, Guildford, Surrey (GB)

(72) Inventors: Peter Renold, Stein (CH); Jerome Yves Cassayre, Stein (CH); Myriem El Qacemi, Stein (CH); Jagadish Pabba, Goa (IN); Thomas Pitterna, Stein (CH)

(73) Assignees: Syngenta Limited, Guildford, Surrey (GB); Syngenta Crop Protection LLC, Greensboro, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 14/574,877

(22) Filed: Dec. 18, 2014

(65) Prior Publication Data

US 2015/0111944 A1    Apr. 23, 2015

Related U.S. Application Data

(63) Continuation of application No. 13/379,812, filed as application No. PCT/EP2010/058207 on Jun. 11, 2010, now Pat. No. 8,946,447.

(30) Foreign Application Priority Data

Jun. 22, 2009  (GB) .................................. 0910767.3
Jun. 22, 2009  (GB) .................................. 0910768.1
Jul. 24, 2009  (WO) ................ PCT/EP2009/059563
Feb. 17, 2010  (EP) .................................... 10153810

(51) Int. Cl.
| | |
|---|---|
| C07D 409/12 | (2006.01) |
| A01N 43/36 | (2006.01) |
| C07D 207/20 | (2006.01) |
| C07D 401/04 | (2006.01) |
| C07D 403/04 | (2006.01) |
| C07D 409/14 | (2006.01) |
| C07F 7/08 | (2006.01) |

(52) U.S. Cl.
CPC ............ C07D 409/12 (2013.01); A01N 43/36 (2013.01); C07D 207/20 (2013.01); C07D 401/04 (2013.01); C07D 403/04 (2013.01); C07D 409/14 (2013.01); C07F 7/0812 (2013.01)

(58) Field of Classification Search
CPC ............................. C07D 409/12; A01N 43/36
See application file for complete search history.

(56) References Cited

U.S. PATENT DOCUMENTS

2013/0109757 A1    5/2013  Moradi et al.

FOREIGN PATENT DOCUMENTS

| | | |
|---|---|---|
| CN | 1930136 A | 3/2007 |
| JP | 2007091708 | 12/2007 |
| JP | 2008133273 A2 | 6/2008 |
| JP | 2010254629 | 4/2009 |
| WO | 2007079162 A1 | 7/2007 |
| WO | 2007080131 A2 | 7/2007 |
| WO | 2008154528 A2 | 12/2008 |
| WO | 2009011227 | 3/2009 |
| WO | 2009072621 A1 | 6/2009 |
| WO | 2009080250 A2 | 7/2009 |
| WO | 2009097992 | 8/2009 |
| WO | 2010084067 | 1/2010 |
| WO | 2010086225 | 1/2010 |
| WO | 2010020522 | 2/2010 |
| WO | 2010108733 | 2/2010 |
| WO | 2010025998 | 3/2010 |
| WO | 2010133336 | 5/2010 |
| WO | 2011101229 | 1/2011 |
| WO | 2011101402 | 2/2011 |
| WO | 2011104087 | 2/2011 |
| WO | 2011104088 | 2/2011 |
| WO | 2011104089 | 2/2011 |
| WO | 2011054871 | 5/2011 |
| WO | 2011073444 | 6/2011 |

(Continued)

OTHER PUBLICATIONS

International Search Report and Written Opinion for International Patent Application No. PCT/EP2010/058207 mailed Sep. 22, 2010.
Minakuchi et al., Biorganic & Medicinal Chemistry Letters, 16 (2006), p. 4080-4084.

(Continued)

*Primary Examiner* — Robert Havlin
(74) *Attorney, Agent, or Firm* — R. Kody Jones

(57) ABSTRACT

The invention relates to compounds of formula (I):

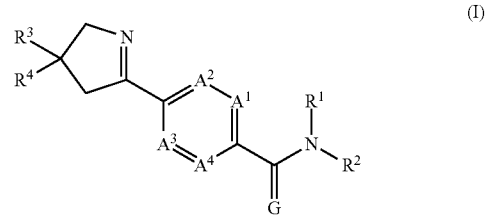

where $A^1$, $A^2$, $A^3$, $A^4$, G, $R^1$, $R^2$, $R^3$ and $R^4$ are as defined in claim 1; or a salt or N-oxide thereof.

Furthermore, the present invention relates to processes and intermediates for preparing compounds of formula (I), to insecticidal, acaricidal, nematicidal and molluscicidal compositions comprising the compounds of formula (I) and to methods of using the compounds of formula (I) to control insect, acarine, nematode and mollusc pests.

8 Claims, No Drawings

(56) References Cited

FOREIGN PATENT DOCUMENTS

| | | |
|---|---|---|
| WO | 2011075591 | 6/2011 |
| WO | 2011154433 | 6/2011 |
| WO | 2011154434 | 6/2011 |

OTHER PUBLICATIONS

Machine Translation of JP 2008133273 (2008).
Machine Translation of JP 2007091708 (2007).
International Preliminary Report on Patentability for International Patent Application No. PCT/EP2010/058207 mailed Jan. 4, 2012.

INSECTICIDAL COMPOUNDS

This application is a continuation of U.S. patent application Ser. No. 13/379,812, filed Mar. 14, 2012, which was a national phase of International Application No. PCT/EP2010/058207, filed Jun. 11, 2010, which claims priority to GB 0910768.1 filed Jun. 22, 2009, GB 0910767.3 filed Jun. 22, 2009, PCT/EP2009/059563 filed Jul. 24, 2009, and EP 10153810.6 filed Feb. 17, 2010, the contents of which are incorporated herein by reference.

The present invention relates to certain dihydro-pyrrole derivatives with a four-membered ring as terminal group, to processes and intermediates for preparing these derivatives, to insecticidal, acaricidal, nematicidal and molluscicidal compositions comprising these derivatives and to methods of using these derivatives to control insect, acarine, nematode and mollusc pests.

Certain dihydro-pyrrole derivatives with insecticidal properties are disclosed in, for example, JP 2007/091708 and JP 2008/133273.

It has now surprisingly been found that dihydro-pyrrole derivatives with a four-membered ring as terminal group have insecticidal properties.

The present invention therefore provides a compound of formula (I)

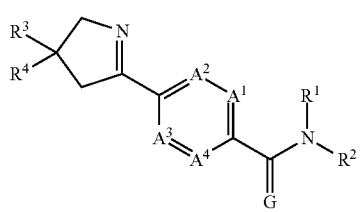

where
$A^1$, $A^2$, $A^3$ and $A^4$ are independently of each other C—H, C—$R^5$ or nitrogen;
G is oxygen or sulfur;
$R^1$ is hydrogen, $C_1$-$C_8$alkyl, $C_1$-$C_8$alkoxy-, $C_1$-$C_8$alkylcarbonyl- or $C_1$-$C_8$alkoxycarbonyl-;
$R^2$ is a group of formula (II)

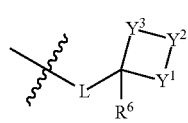

where
L is a single bond or $C_1$-$C_6$alkylene; and
$Y^1$, $Y^2$ and $Y^3$ are independently of another $CR^8R^9$, C=O, C=N—$OR^{10}$, N—$R^{10}$, S, SO, $SO_2$, S=N—$R^{10}$ or SO=N—$R^{10}$, provided that at least one of $Y^1$, $Y^2$ or $Y^3$ is not $CR^8R^9$, C=O or C=N—$OR^{10}$;
$R^3$ is $C_1$-$C_8$haloalkyl;
$R^4$ is aryl or aryl substituted by one to five $R^7$, or heteroaryl or heteroaryl substituted by one to five $R^7$;
each $R^5$ is independently halogen, cyano, nitro, $C_1$-$C_8$alkyl, $C_1$-$C_8$haloalkyl, $C_1$-$C_8$alkenyl, $C_1$-$C_8$haloalkenyl, $C_1$-$C_8$alkynyl, $C_1$-$C_8$haloalkynyl, $C_3$-$C_{10}$cycloalkyl, $C_1$-$C_8$alkoxy-, $C_1$-$C_8$haloalkoxy-, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl- or $C_1$-$C_8$haloalkylsulfonyl-, or
two $R^5$ on adjacent carbon atoms together form a —CH=CH—CH=CH— bridge;
$R^6$ is hydrogen or $C_1$-$C_8$alkyl;
each $R^7$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, hydroxy, $C_1$-$C_8$alkoxy-, $C_1$-$C_8$haloalkoxy-, mercapto, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, $C_1$-$C_8$haloalkylsulfonyl-, $C_1$-$C_8$alkylcarbonyl-, $C_1$-$C_8$alkoxycarbonyl-, aryl or aryl substituted by one to five $R^{11}$, or heterocyclyl or heterocyclyl substituted by one to five $R^{11}$;
each $R^8$ and $R^9$ is independently hydrogen, halogen, $C_1$-$C_8$alkyl or $C_1$-$C_8$haloalkyl;
each $R^{10}$ is independently hydrogen, cyano, $C_1$-$C_8$alkyl, $C_1$-$C_8$haloalkyl, $C_1$-$C_8$alkylcarbonyl-, $C_1$-$C_8$haloalkylcarbonyl-, $C_1$-$C_8$alkoxycarbonyl-, $C_1$-$C_8$haloalkoxycarbonyl-, $C_1$-$C_8$alkylsulfonyl-, $C_1$-$C_8$haloalkylsulfonyl-, aryl-$C_1$-$C_4$alkylene- or aryl-$C_1$-$C_4$alkylene- where the aryl moiety is substituted by one to three $R^{12}$, or heteroaryl-$C_1$-$C_4$alkylene- or heteroaryl-$C_1$-$C_4$alkylene- where the heteroaryl moiety is substituted by one to three $R^{12}$;
each $R^{11}$ and $R^{12}$ is independently halogen, cyano, nitro, $C_1$-$C_8$alkyl, $C_1$-$C_8$haloalkyl, $C_1$-$C_8$alkoxy-, $C_1$-$C_8$haloalkoxy- or $C_1$-$C_8$alkoxycarbonyl-; or a salt or N-oxide thereof.

The compounds of formula (I) may exist in different geometric or optical isomers or tautomeric forms. This invention covers all such isomers and tautomers and mixtures thereof in all proportions as well as isotopic forms such as deuterated compounds.

The compounds of the invention may contain one or more asymmetric carbon atoms, for example, at the —$CR^3R^4$— group, and may exist as enantiomers (or as pairs of diastereoisomers) or as mixtures of such.

Alkyl groups (either alone or as part of a larger group, such as alkoxy-, alkylthio-, alkylsulfinyl-, alkylsulfonyl-, alkylcarbonyl- or alkoxycarbonyl-) can be in the form of a straight or branched chain and are, for example, methyl, ethyl, propyl, prop-2-yl, butyl, but-2-yl, 2-methyl-prop-1-yl or 2-methyl-prop-2-yl. The alkyl groups are, unless indicated to the contrary, preferably $C_1$-$C_6$, more preferably $C_1$-$C_4$, most preferably $C_1$-$C_3$ alkyl groups.

Alkylene groups can be in the form of a straight or branched chain and are, for example, —$CH_2$—, —$CH_2$—$CH_2$—, —CH($CH_3$)—, —$CH_2$—$CH_2$—$CH_2$—, —CH($CH_3$)—$CH_2$—, or —CH($CH_2CH_3$)—. The alkylene groups are, unless indicated to the contrary, preferably $C_1$-$C_3$, more preferably $C_1$-$C_2$, most preferably $C_1$ alkylene groups.

Alkenyl groups can be in the form of straight or branched chains, and can be, where appropriate, of either the (E)- or (Z)-configuration. Examples are vinyl and allyl. The alkenyl groups are, unless indicated to the contrary, preferably $C_2$-$C_6$, more preferably $C_2$-$C_4$, most preferably $C_2$-$C_3$ alkenyl groups.

Alkynyl groups can be in the form of straight or branched chains. Examples are ethynyl and propargyl. The alkynyl groups are, unless indicated to the contrary, preferably $C_2$-$C_6$, more preferably $C_2$-$C_4$, most preferably $C_2$-$C_3$ alkynyl groups.

Halogen is fluorine, chlorine, bromine or iodine.

Haloalkyl groups (either alone or as part of a larger group, such as haloalkoxy-, haloalkylthio-, haloalkylsulfinyl-, haloalkylsulfonyl-, haloalkylcarbonyl- or haloalkoxycarbonyl-) are alkyl groups which are substituted by one or more of the same or different halogen atoms and are, for example, difluoromethyl, trifluoromethyl, chlorodifluoromethyl or 2,2,2-trifluoro-ethyl.

Haloalkenyl groups are alkenyl groups which are substituted by one or more of the same or different halogen atoms and are, for example, 2,2-difluoro-vinyl or 1,2-dichloro-2-fluoro-vinyl.

Haloalkynyl groups are alkynyl groups which are substituted by one or more of the same or different halogen atoms and are, for example, 1-chloro-prop-2-ynyl.

Cycloalkyl groups can be in mono- or bi-cyclic form and are, for example, cyclopropyl, cyclobutyl, cyclohexyl and bicyclo[2.2.1]heptan-2-yl. The cycloalkyl groups are, unless indicated to the contrary, preferably $C_3$-$C_8$, more preferably $C_3$-$C_6$ cycloalkyl groups.

Aryl groups are aromatic ring systems which can be in mono-, bi- or tricyclic form. Examples of such rings include phenyl, naphthyl, anthracenyl, indenyl or phenanthrenyl. Preferred aryl groups are phenyl and naphthyl, phenyl being most preferred. Where an aryl moiety is said to be substituted, the aryl moiety is, unless indicated to the contrary, preferably substituted by one to four substituents, most preferably by one to three substituents.

Heteroaryl groups are aromatic ring system containing at least one heteroatom and consisting either of a single ring or of two or more fused rings. Preferably, single rings will contain up to three heteroatoms and bicyclic systems up to four heteroatoms which will preferably be chosen from nitrogen, oxygen and sulfur. Examples of monocyclic groups include pyridyl, pyridazinyl, pyrimidinyl, pyrazinyl, pyrrolyl, pyrazolyl, imidazolyl, triazolyl, furanyl, thiophenyl, oxazolyl, isoxazolyl, oxadiazolyl, thiazolyl, isothiazolyl and thiadiazolyl. Examples of bicyclic groups include quinolinyl, cinnolinyl, quinoxalinyl, indolyl, indazolyl, benzimidazolyl, benzothiophenyl and benzothiazolyl. Monocyclic heteroaryl groups are preferred, pyridyl being most preferred. Where a heteroaryl moiety is said to be substituted, the heteroaryl moiety is, unless indicated to the contrary, preferably substituted by one to four substituents, most preferably by one to three substituents.

Heterocyclyl groups are defined to include heteroaryl groups and in addition their unsaturated or partially unsaturated analogues. Examples of monocyclic groups include thietanyl, pyrrolidinyl, tetrahydrofuranyl, [1,3]dioxolanyl, piperidinyl, piperazinyl, [1,4]dioxanyl, and morpholinyl or their oxidised versions such as 1-oxo-thietanyl and 1,1-dioxo-thietanyl. Examples of bicyclic groups include 2,3-dihydro-benzofuranyl, benzo[1,3]dioxolanyl, and 2,3-dihydro-benzo[1,4]dioxinyl. Where a heterocyclyl moiety is said to be substituted, the heterocyclyl moiety is, unless indicated to the contrary, preferably substituted by one to four substituents, most preferably by one to three substituents.

Preferred values of $A^1$, $A^2$, $A^3$, $A^4$, G, $R^1$, $R^2$, $R^3$, $R^4$, L, $Y^1$, $Y^2$, $Y^3$, $R^5$, $R^6$, $R^7$, $R^8$, $R^9$, $R^{10}$, $R^{11}$, $R^{12}$, $R^{13}$ and m are, in any combination, as set out below.

Preferably no more than two of $A^1$, $A^2$, $A^3$ and $A^4$ are nitrogen.

Preferably $A^1$ is C—H or C—$R^5$, most preferably $A^1$ is C—$R^5$.

Preferably $A^2$ is C—H or C—$R^5$, most preferably $A^2$ is C—H.

Preferably $A^3$ is C—H or C—$R^5$, most preferably $A^3$ is C—H.

Preferably $A^4$ is C—H or C—$R^5$, most preferably $A^4$ is C—H.

In one preferred group of compounds $A^1$, $A^2$, $A^3$ and $A^4$ are independently of each other C—H or C—$R^5$.

In one preferred group of compounds $A^1$ is C—$R^5$, $A^2$ is C—H, $A^3$ is C—H or nitrogen and $A^4$ is C—H or nitrogen.

In another preferred group of compounds $A^1$ is C—$R^5$, $A^2$ is C—H, $A^3$ is C—H or nitrogen and $A^4$ is C—H.

In a further preferred group of compounds $A^1$ is C—$R^5$, $A^2$ is C—H, $A^3$ is C—H and $A^4$ is C—H.

Preferably G is oxygen.

Preferably $R^1$ is hydrogen, methyl, ethyl, methylcarbonyl- or methoxycarbonyl-, more preferably hydrogen, methyl or ethyl, most preferably hydrogen.

Preferably $R^2$ is a group of formula (IIa)

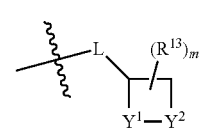

(IIa)

where
L is a single bond, methylene, ethylene or propylene,
$R^{13}$ is $C_1$-$C_8$alkyl,
m is 0, 1, 2, 3, 4, or 5, and
one of $Y^1$ and $Y^2$ is S, SO, $SO_2$, S=N—$R^{10}$, SO=N—$R^{10}$ or C=N—$OR^{10}$, e.g. S, SO, $SO_2$, S=N—$R^{10}$ or SO=N—$R^{10}$, e.g. S, SO, $SO_2$ or C=N—$OR^{10}$, e.g. S, SO or $SO_2$, and the other is $CH_2$ in which each H may be replaced by $R^{13}$.

More preferably $R^2$ is a group of formula (IIb)

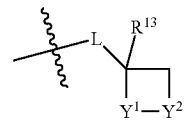

(IIb)

where
L is a single bond, methylene, ethylene or propylene,
$R^{13}$ is hydrogen or $C_1$-$C_8$alkyl, e.g. $C_1$-$C_8$alkyl, and
one of $Y^1$ and $Y^2$ is S, SO, $SO_2$, S=N—$R^{10}$, SO=N—$R^{10}$ or C=N—$OR^{10}$, e.g. S, SO, $SO_2$, S=N—$R^{10}$ or SO=N—$R^{10}$, e.g. S, SO, $SO_2$ or C=N—$OR^{10}$, e.g. S, SO or $SO_2$, and the other is $CH_2$.

More preferably $R^2$ is a group of formula (IIc)

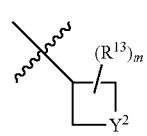

(IIc)

where
$R^{13}$ is $C_1$-$C_8$alkyl, preferably methyl,
m is 0, 1, 2, 3, 4, or 5, and $Y^2$ is S, SO, SO$_2$, S=N—R$^{10}$, SO=N—R$^{10}$ or C=N—OR$^{10}$, e.g. S, SO, SO$_2$ or C=N—OR$^{10}$, e.g. S, SO or SO$_2$.

Even more preferably R$^2$ is a group of formula (IId)

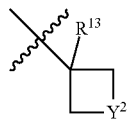

(IId)

where

R$^{13}$ is hydrogen or C$_1$-C$_8$alkyl, e.g. C$_1$-C$_8$alkyl, e.g. hydrogen or methyl, and $Y^2$ is S, SO, SO$_2$, S=N—R$^{10}$, SO=N—R$^{10}$ or C=N—OR$^{10}$, e.g. S, SO, SO$_2$ or C=N—OR$^{10}$, e.g. S, SO or SO$_2$, Most preferably R$^2$ is thietan-3-yl-, 1-oxo-thietan-3-yl-, 1,1-dioxo-thietan-3-yl- or 3-methyl-thietan-3-yl-.

In another preferred group of compounds R$^2$ is a group of formula (IIc')

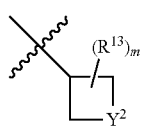

(IIc')

where

R$^{13}$ is C$_1$-C$_8$alkyl, m is 0, 1, 2, 3, 4, or 5, and $Y^2$ is S, SO, SO$_2$, S=N—R$^{10}$ or SO=N—R$^{10}$.

In another group of preferred compounds R$^2$ is a group of formula (IId')

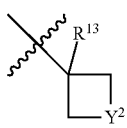

(IId')

where

R$^{13}$ is C$_1$-C$_8$alkyl, and $Y^2$ is S, SO, SO$_2$, S=N—R$^{10}$ or SO=N—R$^{10}$.

Preferably R$^3$ is chlorodifluoromethyl or trifluoromethyl, most preferably trifluoromethyl.

Preferably R$^4$ is phenyl or phenyl substituted by one to five R$^7$, more preferably phenyl substituted by one to three R$^7$, even more preferably R$^4$ is 3,5-dibromo-phenyl-, 3,5-dichloro-phenyl-, 3,5-bis-(trifluoromethyl)-phenyl-, 3,4-dichloro-phenyl-, 3,4,5-trichloro-phenyl- or 3-trifluoromethyl-phenyl-, most preferably 3,5-dichloro-phenyl.

Preferably L is a single bond, methylene, ethylene or propylene.

More preferably L is methylene or a single bond.

Even more preferably L is a single bond.

Preferably $Y^1$ is CR$^8$R$^9$, more preferably CH$_2$.

Preferably $Y^2$ is S, SO, SO$_2$, S=N—R$^{10}$, SO=N—R$^{10}$, or C=N—OR$^{10}$, e.g. S, SO, SO$_2$, S=N—R$^{10}$ or SO=N—R$^{10}$, more preferably S, SO, SO$_2$, S=N—C≡N, SO=NH, SO=N—C≡N or C=N—OR$^{10}$ e.g. S, SO, SO$_2$, S=N—C≡N, SO=NH or SO=N—C≡N, most preferably S, SO, SO$_2$ or C=N—OR$^{10}$, e.g. S, SO or SO$_2$.

Preferably $Y^3$ is CR$^8$R$^9$, more preferably CH$_2$.

Preferably each R$^5$ is independently halogen, C$_1$-C$_8$alkyl, C$_1$-C$_8$haloalkyl or C$_1$-C$_8$alkenyl, or two R$^5$ on adjacent carbon atoms together form a —CH=CH—CH=CH— bridge, more preferably each R$^5$ is independently bromo, chloro, fluoro, methyl, trifluoromethyl or vinyl, or two R$^5$ on adjacent carbon atoms, preferably R$^5$ on A$^1$ and A$^2$, together form a —CH=CH—CH=CH— bridge, most preferably each R$^5$ is independently methyl.

Preferably R$^6$ is methyl or hydrogen.

Preferably each R$^7$ is independently halogen, cyano, C$_1$-C$_8$alkyl, C$_1$-C$_8$haloalkyl or C$_1$-C$_8$alkoxy-, more preferably bromo, chloro, fluoro, cyano, methyl, trifluoromethyl, methoxy or trifluoromethoxy, preferably bromo, chloro or trifluoromethyl, most preferably bromo or chloro.

Preferably each R$^8$ is independently hydrogen or C$_1$-C$_8$alkyl, more preferably hydrogen or methyl, most preferably hydrogen.

Preferably each R$^9$ is independently hydrogen or C$_1$-C$_8$alkyl, more preferably hydrogen or methyl, most preferably hydrogen.

Preferably each R$^{10}$ is independently methyl, hydrogen or cyano, e.g. hydrogen or cyano, preferably methyl or hydrogen, e.g. hydrogen.

Preferably each R$^{11}$ is independently bromo, chloro, fluoro, cyano, nitro, methyl, ethyl, trifluoromethyl, methoxy, difluoromethoxy or trifluoromethoxy, more preferably bromo, chloro, fluoro, nitro or methyl, most preferably chloro, fluoro or methyl.

Preferably each R$^{12}$ is independently bromo, chloro, fluoro, cyano, nitro, methyl, ethyl, trifluoromethyl, methoxy, difluoromethoxy or trifluoromethoxy, more preferably bromo, chloro, fluoro, nitro or methyl, most preferably chloro, fluoro or methyl.

Preferably each R$^{13}$ is independently methyl.

Preferably m is 0 or 1, most preferably 0.

A group of preferred compounds are those wherein A$^1$, A$^2$, A$^3$ and A$^4$ are independently of each other C—H or C—R$^5$, preferably A$^1$ is C—R$^5$, A$^2$ is C—H, A$^3$ is C—H or nitrogen and A$^4$ is C—H or nitrogen;

G is oxygen;

R$^1$ is hydrogen, methyl, ethyl, methylcarbonyl- or methoxycarbonyl-;

R$^2$ is a group of formula (IIa)

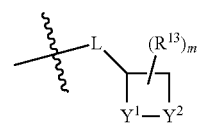

(IIa)

where

L is a single bond, methylene methylene, ethylene or propylene, m is 0, 1, 2, 3, 4, or 5, and one of $Y^1$ and $Y^2$ is S, SO, SO$_2$, S=N—R$^{10}$, SO=N—R$^{10}$ or C=N—OR$^{10}$, and the other is CH$_2$ in which each H may be replaced by R$^{13}$.

R$^3$ is C$_1$-C$_8$ haloalkyl;

R$^4$ is phenyl substituted by one to three R$^7$;

each R$^5$ is independently halogen, C$_1$-C$_8$alkyl, C$_1$-C$_8$haloalkyl or C$_1$-C$_8$alkenyl, or two R$^5$ on adjacent carbon atoms together form a —CH=CH—CH=CH— bridge;

each $R^7$ is independently halogen, cyano, $C_1$-$C_8$alkyl, $C_1$-$C_8$haloalkyl or $C_1$-$C_8$alkoxy-;
each $R^{10}$ is independently methyl, hydrogen or cyano;
$R^{13}$ is $C_1$-$C_8$alkyl, Another group of preferred compounds are those wherein
$A^1$, $A^2$, $A^3$ and $A^4$ are independently of each other C—H or C—$R^5$, preferably $A^1$ is C—$R^5$, $A^2$ is C—H, $A^3$ is C—H and $A^4$ is C—H;
G is oxygen;
$R^1$ is hydrogen, methyl or ethyl;
$R^2$ is a group of formula (IIb)

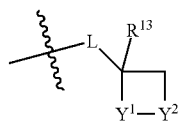

(IIb)

where
L is a single bond methylene, ethylene or propylene,
one of $Y^1$ and $Y^2$ is S, SO, $SO_2$, S=N—$R^{10}$, SO=N—$R^{10}$ or C=N—$OR^{10}$ and the other is $CH_2$;
$R^3$ is chlorodifluoromethyl or trifluoromethyl;
$R^4$ is 3,5-dibromo-phenyl-, 3,5-dichloro-phenyl-, 3,5-bis-(trifluoromethyl)-phenyl-, 3,4-dichloro-phenyl-, 3,4,5-trichloro-phenyl- or 3-trifluoromethyl-phenyl-;
each $R^5$ is independently bromo, chloro, fluoro, methyl, trifluoromethyl or vinyl, or
two $R^5$ on adjacent carbon atoms together form a —CH=CH—CH=CH— bridge;
each $R^{10}$ is independently methyl or hydrogen;
$R^{13}$ is hydrogen or $C_1$-$C_8$alkyl.

Yet another group of preferred compounds are those wherein
$A^1$, $A^2$, $A^3$ and $A^4$ are independently of each other C—H or C—$R^5$, preferably $A^1$ is C—$R^5$, $A^2$ is C—H, $A^3$ is C—H and $A^4$ is C—H;
G is oxygen;
$R^1$ is hydrogen;
$R^2$ is a group of formula (IIc)

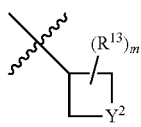

(IIc)

where
m is 0, 1, 2, 3, 4, or 5, and
$Y^2$ is S, SO, $SO_2$, or C=N—$OR^{10}$;
$R^3$ is chlorodifluoromethyl or trifluoromethyl;
$R^4$ is 3,5-dibromo-phenyl-, 3,5-dichloro-phenyl-, 3,5-bis-(trifluoromethyl)-phenyl-, 3,4-dichloro-phenyl-, 3,4,5-trichloro-phenyl- or 3-trifluoromethyl-phenyl-;
each $R^5$ is independently bromo, chloro, fluoro, methyl, trifluoromethyl or vinyl, or two $R^5$ on adjacent carbon atoms together form a —CH=CH—CH=CH— bridge;
each $R^{10}$ is independently methyl or hydrogen;
$R^{13}$ is methyl.

A further group of preferred compounds are those wherein
$A^1$ is C—$R^5$, $A^2$ is C—H, $A^3$ is C—H and $A^4$ is C—H;
G is oxygen;
$R^1$ is hydrogen;
$R^2$ is a group of formula (IId)

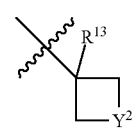

(IId)

where
$Y^2$ is S, SO, $SO_2$;
$R^3$ is trifluoromethyl;
$R^4$ is 3,5-dichloro-phenyl;
each $R^5$ is independently methyl;
$R^{13}$ is hydrogen or methyl.

In one preferred embodiment there is provided a compound of formula (Ia)

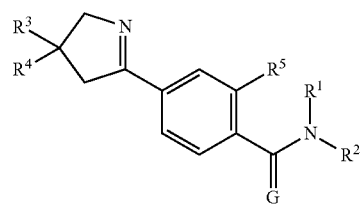

(Ia)

where G, $R^1$, $R^2$, $R^3$, $R^4$ and $R^5$ are as defined for a compound of formula (I); or a salt or N-oxide thereof. The preferred values of G, L, $R^1$, $R^2$, $R^3$, $R^4$, $Y^1$, $Y^2$, $Y^3$, $R^5$, $R^6$, $R^7$, $R^8$, $R^9$, $R^{10}$, $R^{11}$, $R^{12}$, $R^{13}$ and m are as defined for a compound of formula (I).

In one preferred embodiment there is provided a compound of formula (Ib)

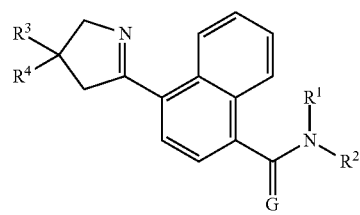

(Ib)

where G, $R^1$, $R^2$, $R^3$ and $R^4$ are as defined for a compound of formula (I); or a salt or N-oxide thereof. The preferred values of G, L, $R^1$, $R^2$, $R^3$, $R^4$, $Y^1$, $Y^2$, $Y^3$, $R^6$, $R^7$, $R^8$, $R^9$, $R^{10}$, $R^{11}$, $R^{12}$, $R^{13}$ and m are as defined for a compound of formula (I).

In one preferred embodiment there is provided a compound of formula (Ic)

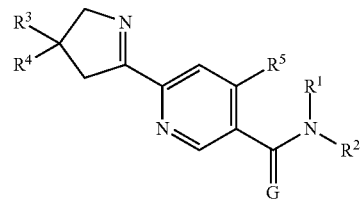

(Ic)

where G, $R^1$, $R^2$, $R^3$, $R^4$ and $R^5$ are as defined for a compound of formula (I); or a salt or N-oxide thereof. The preferred values of G, L, $R^1$, $R^2$, $R^3$, $R^4$, $Y^1$, $Y^2$, $Y^3$, $R^5$, $R^6$, $R^7$, $R^8$, $R^9$, $R^{10}$, $R^{11}$, $R^{12}$, $R^{13}$ and m are as defined for a compound of formula (I).

Certain intermediates are novel and as such form a further aspect of the invention.

One group of novel intermediates are compounds of formula (IA)

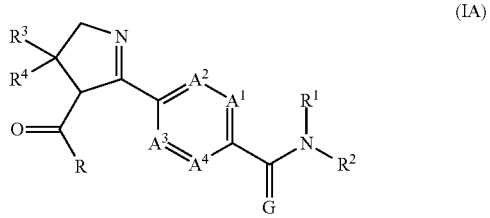

(IA)

wherein $A^1$, $A^2$, $A^3$, $A^4$, $R^1$, $R^2$, $R^3$ and $R^4$ are as defined for a compound of formula (I); G is oxygen and R is $C_1$-$C_6$alkoxy. The preferences for $A^1$, $A^2$, $A^3$, $A^4$, $R^1$, $R^2$, $R^3$ and $R^4$ are the same as the preferences set out for the corresponding substituents of a compound of formula (I).

A further group of novel intermediates are compounds of formula (VA)

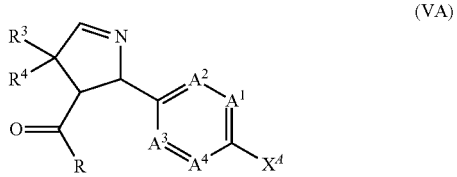

(VA)

wherein $A^1$, $A^2$, $A^3$, $A^4$, $R^3$ and $R^4$ are as defined for a compound of formula (I); R is $C_1$-$C_6$alkoxy; and $X^A$ is a leaving group such as a halogen atom, preferably bromine or chlorine, more preferably bromine. The preferences for $A^1$, $A^2$, $A^3$, $A^4$, $R^3$ and $R^4$ are the same as the preferences set out for the corresponding substituents of a compound of formula (I).

A further group of novel intermediates are compounds of formula (XIA)

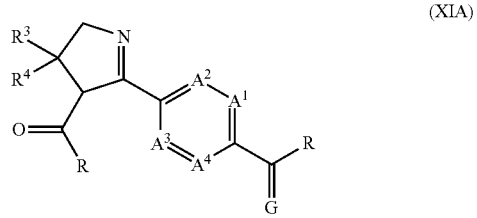

(XIA)

wherein $A^1$, $A^2$, $A^3$, $A^4$, $R^3$ and $R^4$ are as defined for a compound of formula (I); each R is independently $C_1$-$C_6$alkoxy; G is oxygen and $X^A$ is a leaving group such as a halogen atom, preferably bromine or chlorine, more preferably bromine. The preferences for $A^1$, $A^2$, $A^3$, $A^4$, $R^3$ and $R^4$ are the same as the preferences set out for the corresponding substituents of a compound of formula (I).

A further group of novel intermediates are compounds of formula (XVII)

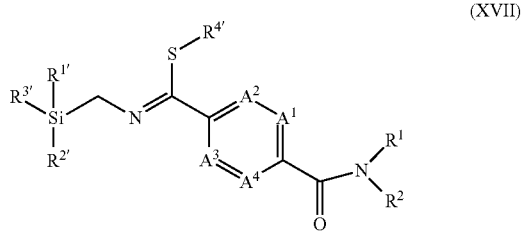

(XVII)

wherein $A^1$, $A^2$, $A^3$, $A^4$, $R^1$ and $R^2$ are as defined for a compound of formula (I), $R^{1'}$, $R^{2'}$ and $R^{3'}$ are each independently optionally substituted alkyl or optionally substituted phenyl, preferably $C_1$-$C_8$ alkyl, $C_1$-$C_8$ haloalkyl, phenyl or phenyl optionally substituted with one to five groups independently selected from halogen and $C_1$-$C_8$ alkyl, $R^4$, is optionally substituted phenyl, optionally substituted alkyl, preferably $C_1$-$C_8$ alkyl or $C_1$-$C_8$ haloalkyl. The preferences for $A^1$, $A^2$, $A^3$, $A^4$, $R^1$ and $R^2$ are the same as the preferences set out for the corresponding substituents of a compound of formula (I).

A further group of novel intermediates are compounds of formula (XX)

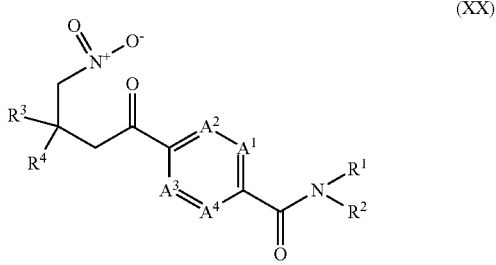

(XX)

wherein $A^1$, $A^2$, $A^3$, $A^4$, $R^1$, $R^2$, $R^3$ and $R^4$ are as defined for a compound of formula (I). The preferences for $A^1$, $A^2$, $A^3$, $A^4$, $R^1$, $R^2$, $R^3$ and $R^4$ are the same as the preferences set out for the corresponding substituents of a compound of formula (I).

A further group of novel intermediates are compounds of formula (XXIV)

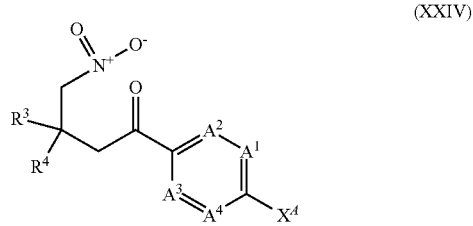

(XXIV)

wherein $A^1$, $A^2$, $A^3$, $A^4$, $R^3$ and $R^4$ are as defined for a compound of formula (I); and $X^A$ is a leaving group such as a halogen atom, preferably bromine or chlorine, more preferably bromine. The preferences for $A^1$, $A^2$, $A^3$, $A^4$, $R^3$ and $R^4$ are the same as the preferences set out for the corresponding substituents of a compound of formula (I).

A further group of novel intermediates are compounds of formula (XXVI)

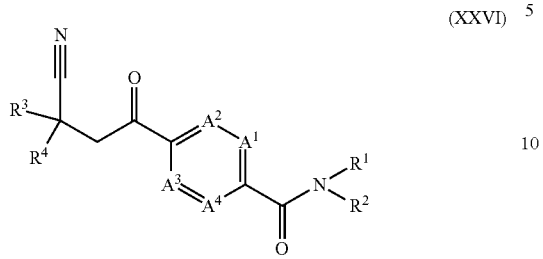

wherein $A^1$, $A^2$, $A^3$, $A^4$, $R^1$, $R^2$, $R^3$ and $R^4$ are as defined for a compound of formula (I); The preferences for $A^1$, $A^2$, $A^3$, $A^4$, $R^1$, $R^2$, $R^3$ and $R^4$ are the same as the preferences set out for the corresponding substituents of a compound of formula (I).

A further group of novel intermediates are compounds of formula (XXVII)

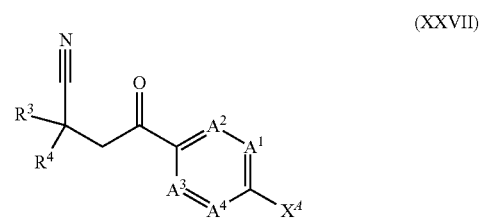

wherein $A^1$, $A^2$, $A^3$, $A^4$, $R^3$ and $R^4$ are as defined for a compound of formula (I); and $X^4$ is a leaving group such as a halogen atom, preferably bromine or chlorine, more preferably bromine. The preferences for $A^1$, $A^2$, $A^3$, $A^4$, $R^3$ and $R^4$ are the same as the preferences set out for the corresponding substituents of a compound of formula (I).

The compounds of the invention may be made by a variety of methods, for example, as shown in Scheme 1.

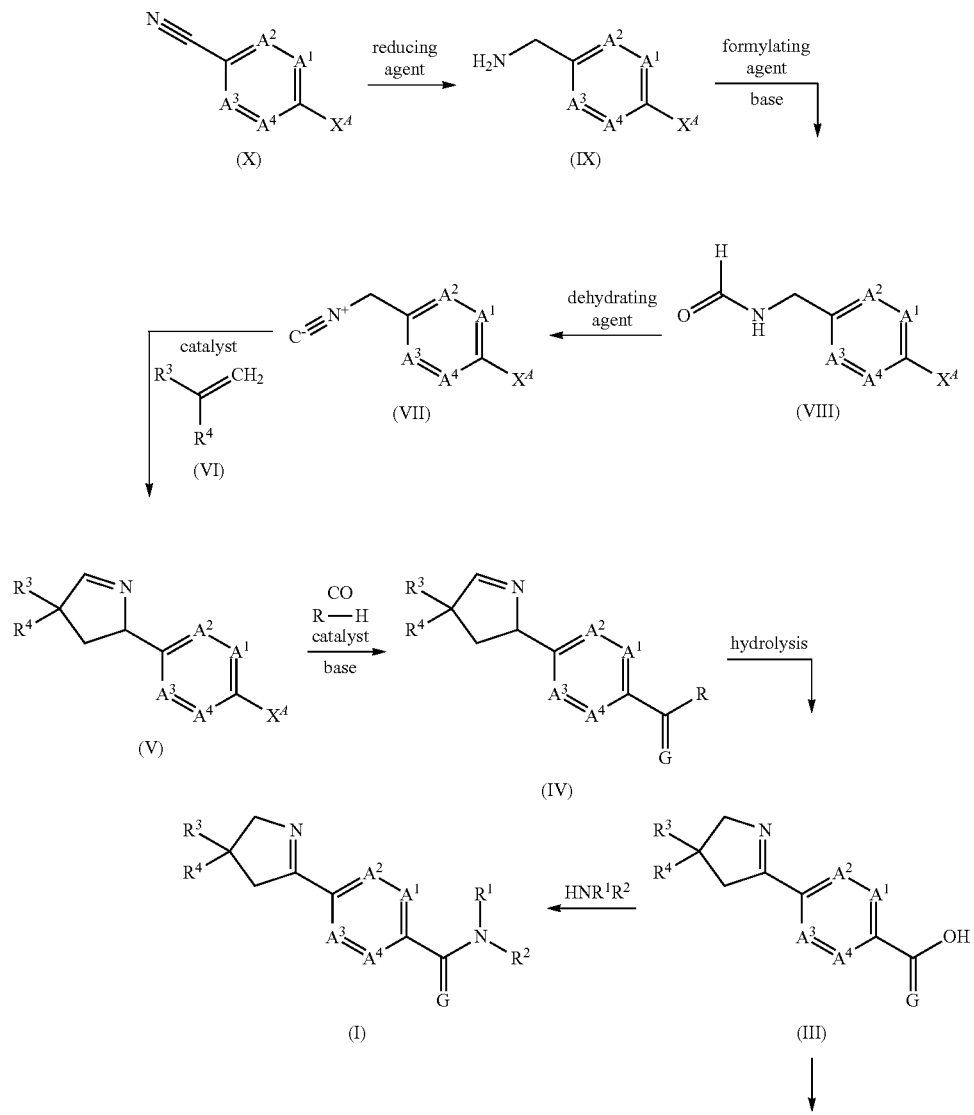

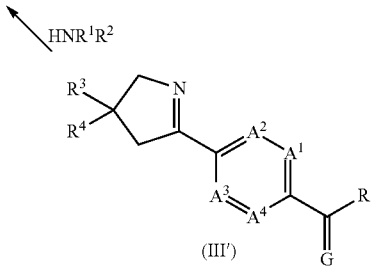

(III')

1) An amine of formula (IX) where $A^1$, $A^2$, $A^3$ and $A^4$ are as defined for a compound of formula (I) and $X^4$ is a leaving group, for example a halogen atom, such as a bromine atom, can be made by reacting a benzonitrile of formula (X) where $A^1$, $A^2$, $A^3$ and $A^4$ are as defined for a compound of formula (I) and $X^4$ is a leaving group, for example a halogen atom, such as a bromine atom, with a reducing agent, for example a metal hydride, such as lithium aluminum hydride, in a solvent, such as an aprotic solvent, such as diethyl ether. The reaction is carried out preferably under a protective atmosphere, such as an argon atmosphere. The reaction is carried out preferably at a temperature of from −20° C. to +100° C., more preferably from 0° C. to 80° C., in particular at 40° C. Benzonitriles of formula (X) are commercially available or can be made by methods known to a person skilled in the art.

2) A formamide of formula (VIII) where $A^1$, $A^2$, $A^3$ and $A^4$ are as defined for a compound of formula (I) and $X^4$ is a leaving group, for example a halogen atom, such as a bromine atom, can be made by reacting an amine of formula (IX) as defined under 1), with a formylating agent, such as ethyl formate, in a solvent, for example an excess of the formylating agent, in the presence of a base, for example an organic base, such as triethylamine. The reaction is carried out preferably at a temperature of from −20° C. to +100° C., more preferably from 20° C. to 90° C., in particular at the reflux temperature of the solvent.

3) An isocyano compound of formula (VII) where $A^1$, $A^2$, $A^3$ and $A^4$ are as defined for a compound of formula (I) and $X^4$ is a leaving group, for example a halogen atom, such as a bromine atom, can be made by reacting a formamide of formula (VIII) as defined under 2), with a dehydrating agent, for example a chlorinating agent, such as phosphorus oxychloride, in a solvent, for example an aprotic solvent, such as dichloromethane. The reaction is carried out preferably at a temperature of from −20° C. to +50° C., more preferably from 0° C. to 50° C., in particular at ambient temperature.

4) A compound of formula (V) where $A^1$, $A^2$, $A^3$, $A^4$, $R^3$ and $R^4$ are as defined for a compound of formula (I) and $X^4$ is a leaving group, for example a halogen atom, such as a bromine atom, can be made by reacting an isocyano compound of formula (VII) as defined under 3), with a vinyl compound of formula (VI) where $R^3$ and $R^4$ are as defined for a compound of formula (I), in the presence of a catalyst, such as copper(I) oxide, in a solvent, for example an aromatic solvent, such as toluene. The reaction is carried out preferably at a temperature of from −20° C. to +200° C., more preferably from 50° C. to 150° C., in particular at 110° C. Vinyl compounds of formula (VI) are known from the literature (for example, from EP 1,731,512) or can be made by methods known to a person skilled in the art.

5) A carboxylic ester of formula (IV) where $A^1$, $A^2$, $A^3$, $A^4$, $R^3$ and $R^4$ are as defined for a compound of formula (I), G is oxygen and R is $C_1$-$C_8$alkoxy, can be made by reacting a compound of formula (V) as defined under 4), with carbon monoxide and an alcohol of formula R—H where R is $C_1$-$C_8$alkoxy, such as ethanol, in the presence of a catalyst, such as bis(triphenylphosphine)palladium(II) dichloride ("Pd(PPh$_3$)$_2$Cl$_2$") or dichloro 1,1'-bis(diphenylphosphino) ferrocene palladium(II) dichloromethane adduct ("Pd(dppf) Cl$_2$"), in the presence of a base, such as pyridine, triethylamine, 4-(dimethylamino)-pyridine ("DMAP"), diisopropylethylamine (Hunig's base) or sodium acetate, and optionally in the presence of a solvent, for example a polar solvent, such as dimethylformamide. The reaction is carried out preferably at a temperature of from −20° C. to +200° C., more preferably from 50° C. to 150° C., in particular at 85° C. The reaction is carried out preferably at a pressure of from 1 to 200 bar, more preferably from 2 to 10 bar, in particular at 6 bar.

6) A carboxylic acid of formula (III) where $A^1$, $A^2$, $A^3$, $A^4$, $R^3$ and $R^4$ are as defined for a compound of formula (I), G is oxygen and R is OH, can be made from a carboxylic ester of formula (IV) as defined under 5), under standard conditions, such as treatment with an alkali hydroxide, such as sodium hydroxide or potassium hydroxide, in a solvent, such as ethanol or tetrahydrofuran, in the presence of water. Another alternative is the treatment of the ester with an acid, such as trifluoroacetic acid, in a solvent, such as dichloromethane, followed by addition of water. The reaction is carried out preferably at a temperature of from −20° C. to +100° C., more preferably from 20° C. to 80° C., in particular at 50° C.

7) An acid halide of formula (III') where $A^1$, $A^2$, $A^3$, $A^4$, $R^3$ and $R^4$ are as defined for a compound of formula (I), G is oxygen and R is Br, Cl or F, can be made from a carboxylic acid of formula (III) as defined under 5), under standard conditions, such as treatment with thionyl chloride or oxalyl chloride, in a solvent, such as dichloromethane. The reaction is carried out preferably at a temperature of from −20° C. to +100° C., more preferably from 0° C. to 50° C., in particular at ambient temperature.

8) A compound of formula (I) where $A^1$, $A^2$, $A^3$, $A^4$, $R^3$ and $R^4$ are as defined for a compound of formula (I) and G is oxygen, can be made by reacting a carboxylic acid of formula (III) or an acid halide of formula (III') where $A^1$, $A^2$, $A^3$, $A^4$, $R^3$ and $R^4$ are as defined for a compound of formula (I) and G is oxygen, with an amine of formula $HNR^1R^2$ where $R^1$ and $R^2$ are as defined for a compound of formula (I). When a carboxylic acid is used, such reactions are usually carried out in the presence of a coupling reagent, such as N,N'-dicyclohexylcarbodiimide ("DCC"), 1-ethyl-3-(3-dimethylamino-propyl)carbodiimide hydrochloride ("EDC") or bis(2-oxo-3-oxazolidinyl)phosphonic chloride ("BOP-Cl"), in the presence of a base, and optionally in the presence of a nucleophilic catalyst. Such reactions are carried out preferably at a temperature of from −20° C. to +200° C., more preferably from 50° C. to 150° C., in particular at 100° C. When an acid halide is used, such reactions are usually carried out in the presence of a base, and optionally in the presence of a nucleophilic catalyst. Alternatively, when an acid halide is used it is possible to conduct the reaction in a biphasic system comprising an organic solvent, preferably ethyl acetate, and an aqueous solvent, preferably a solution of sodium hydrogen carbonate. Such reactions are carried out preferably at a temperature of from −20° C. to +50° C., more preferably from 0° C. to 50° C., in particular at ambient temperature. Suitable nucleophilic catalysts include hydroxybenzotriazole ("HOBT"). Suitable solvents include dimethylacetamide, tetrahydrofuran, dioxane, 1,2-dimethoxyethane, ethyl acetate and toluene. Amines of formula (II) are known from the literature (for example, from WO 2007/080131) or can be made by methods known to a person skilled in the art.

9) A compound of formula (I) where $A^1$, $A^2$, $A^3$, $A^4$, $R^1$, $R^2$, $R^3$ and $R^4$ are as defined for a compound of formula (I) and G is sulfur, can be made by reacting a compound of formula (III) where $A^1$, $A^2$, $A^3$, $A^4$, $R^3$ and $R^4$ are as defined for a compound of formula (I), G is oxygen, or a compound of formula (III') wherein R is Br, Cl or F, or a compound of formula (XI) wherein R is $C_1$-$C_8$alkoxy (see Scheme 2), with a thio-transfer reagent, such as Lawesson's reagent or phosphorus pentasulfide, prior to reacting with the amine of formula $HNR^1R^2$ as described under 8).

Scheme 1a

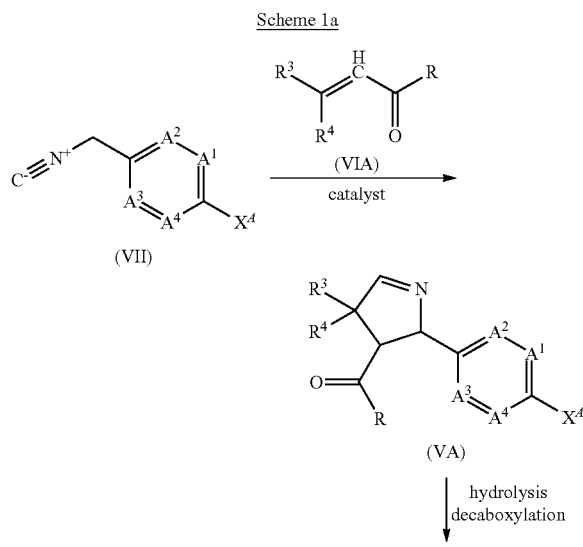

(VII)

(VIA)
catalyst (VA)

hydrolysis
decaboxylation

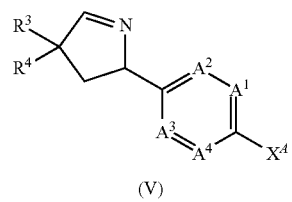

(V)

9a) Alternatively a compound of formula (V) where $A^1$, $A^2$, $A^3$, $A^4$, $R^3$ and $R^4$ are as defined for a compound of formula (I) and $X^A$ is a leaving group, for example a halogen atom, such as a bromine atom can be made by treatment of a compound of formula (VA) where $A^1$, $A^2$, $A^3$, $A^4$, $R^3$ and $R^4$ are as defined for a compound of formula (I) and $X^A$ is a leaving group, for example a halogen atom, such as a bromine atom and R is $C_1$-$C_6$alkoxy under hydrolytic conditions followed by decarboxylation of the acid intermediate. Such conditions are, for example, treatment with an alkali hydroxide, such as sodium hydroxide or potassium hydroxide, in a solvent, such as ethanol or tetrahydrofuran, in the presence of water. Another alternative is the treatment of the ester with an acid, such as trifluoroacetic acid, in a solvent, such as dichloromethane, followed by addition of water. The reaction is carried out preferably at a temperature of from −20° C. to +100° C., more preferably from 20° C. to 80° C., in particular at 50° C.

9b) A compound of formula (VA) as $A^1$, $A^2$, $A^3$, $A^4$, $R^3$ and $R^4$ are as defined for a compound of formula (I) and $X^A$ is a leaving group, for example a halogen atom, such as a bromine atom, can be made by reacting an isocyano compound of formula (VII) as defined under 3), with a vinyl compound of formula (VIA) where $R^3$ and $R^4$ are as defined for a compound of formula (I) and R is $C_1$-$C_6$alkoxy, in the presence of a catalyst, such as copper(I) oxide, in a solvent, for example an aromatic solvent, such as toluene. The reaction is carried out preferably at a temperature of from −20° C. to +200° C., more preferably from 50° C. to 150° C., in particular at 110° C. Vinyl compounds of formula (VIA) are known from the literature (for example, from J. Org. Chem. (2003), 68(15), 5925-5929) or can be made by methods known to a person skilled in the art.

Scheme 2

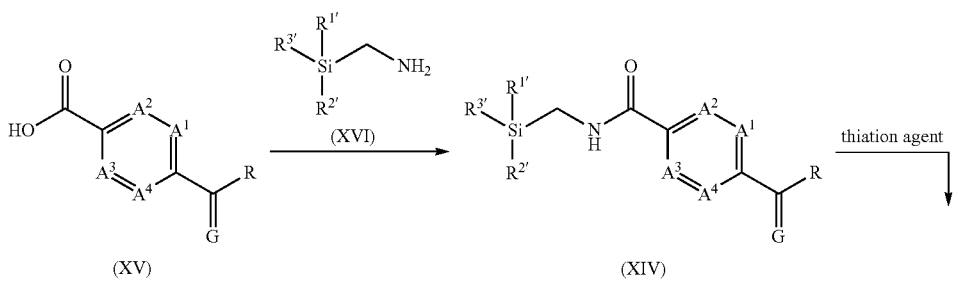

(XV) → (XVI) → (XIV) → thiation agent

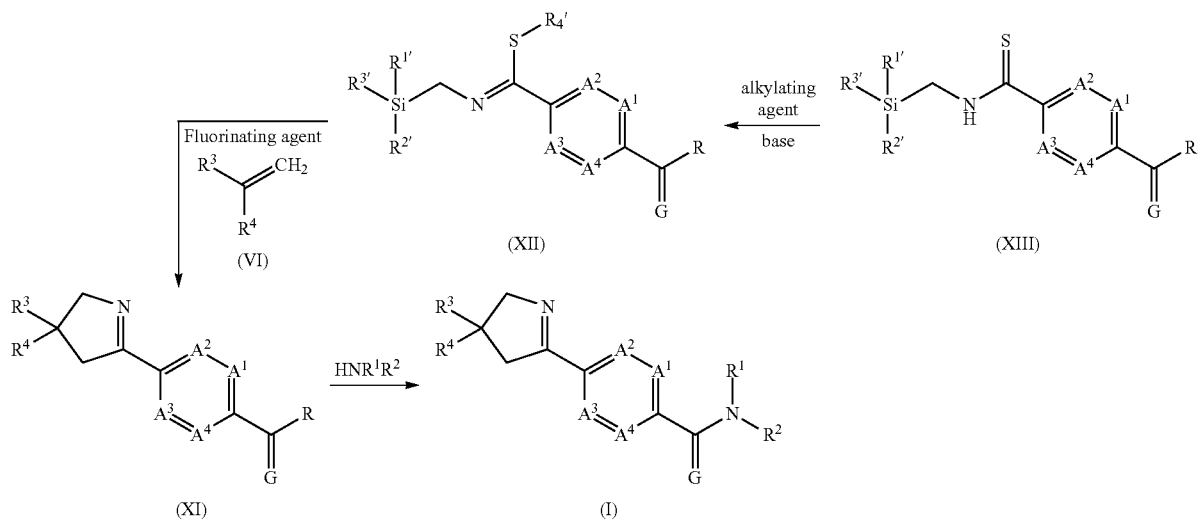

10) A compound of formula (XIV) where $A^1$, $A^2$, $A^3$, $A^4$ are as defined for a compound of formula (I), R is $C_1$-$C_6$alkoxy, $R^{1'}$, $R^{2'}$ and $R^{3'}$ represent optionally substituted alkyl or optionally substituted phenyl and G is oxygen, can be made by reacting a carboxylic acid of formula (XV) where $A^1$, $A^2$, $A^3$, $A^4$ are as defined for a compound of formula (I) and R is $C_1$-$C_6$alkoxy, with an amine (XVI) where $R^{1'}$, $R^{2'}$ and $R^{3'}$ represent optionally substituted alkyl or optionally substituted phenyl. Such reactions are usually carried out in the presence of a coupling reagent, such as N,N'-dicyclohexylcarbodiimide ("DCC"), 1-ethyl-3-(3-dimethylamino-propyl)carbodiimide hydrochloride ("EDC") or bis(2-oxo-3-oxazolidinyl)phosphonic chloride ("BOP-Cl"), in the presence of a base, and optionally in the presence of a nucleophilic catalyst. Such reactions are carried out preferably at a temperature of from −20° C. to +200° C., more preferably from 50° C. to 150° C., in particular at 100° C. Suitable nucleophilic catalysts include hydroxybenzotriazole ("HOBT"). Suitable solvents include dimethylacetamide, tetrahydrofuran, dioxane, 1,2-dimethoxyethane, ethyl acetate and toluene. Amines of formula (XVI) and carboxylic acids of formula (XV) are known from the literature or can be made by methods known to a person skilled in the art.

11) A compound of formula (XIII) where $A^1$, $A^2$, $A^3$, $A^4$ are as defined for a compound of formula (I) R is $C_1$-$C_6$alkoxy, $R^{1'}$, $R^{2'}$ and $R^{3'}$ represent optionally substituted alkyl or optionally substituted phenyl and G is oxygen can be made by reacting a compound of formula (XIV) where $A^1$, $A^2$, $A^3$, $A^4$ are as defined for a compound of formula (I) R is $C_1$-$C_6$alkoxy, $R^{1'}$, $R^{2'}$ and $R^{3'}$ represent optionally substituted alkyl or optionally substituted phenyl and G is oxygen, with a thio-transfer reagent, such as Lawesson's reagent or phosphorus pentasulfide in a solvent, for example an aromatic solvent, such as toluene. The reaction is carried out preferably at a temperature of from −20° C. to +200° C., more preferably from 50° C. to 150° C., in particular at 110° C.

12) A compound of formula (XII) where $A^1$, $A^2$, $A^3$, $A^4$ are as defined for a compound of formula (I) R is $C_1$-$C_6$alkoxy, $R^{1'}$, $R^{2'}$ and $R^{3'}$ represent optionally substituted alkyl or optionally substituted phenyl, $R^{4'}$ represents optionally substituted alkyl and G is oxygen can be made by reacting a compound of formula (XIII) where $A^1$, $A^2$, $A^3$, $A^4$ are as defined for a compound of formula (I) R is $C_1$-$C_6$alkoxy, $R^{1'}$, $R^{2'}$ and $R^{3'}$ represent optionally substituted alkyl or optionally substituted phenyl and G is oxygen with an alkylating agent $R^{4'}$—X where X is a leaving group for example a halogen atom, such as an iodine atom and a base such as sodium carbonate or potassium carbonate in a solvent, such as acetonitrile. The reaction is carried out preferably at a temperature of from −20° C. to +100° C., more preferably from 0° C. to 50° C., in particular at ambient temperature.

13) A compound of formula (XI) where $A^1$, $A^2$, $A^3$, $A^4$, $R^1$, $R^2$, $R^3$ and $R^4$ are as defined for a compound of formula (I), G is oxygen and R is $C_1$-$C_6$alkoxy can be made by reacting a compound of formula (XII) where $A^1$, $A^2$, $A^3$, $A^4$ are as defined for a compound of formula (I) R is $C_1$-$C_6$alkoxy, $R^{1'}$, $R^{2'}$ and $R^{3'}$ represent optionally substituted alkyl or optionally substituted phenyl, $R^{4'}$ represents optionally substituted alkyl and G is oxygen with a vinyl compound of formula (VI) where $R^3$ and $R^4$ are as defined for a compound of formula (I), in the presence of a fluorine reagent such as potassium fluoride or tetrabutylammonium fluoride, in a solvent, for example THF. The reaction is carried out preferably at a temperature of from −20° C. to +500° C., more preferably from 0° C. to 100° C., in particular at ambient temperature. Vinyl compounds of formula (VI) are known from the literature (for example, from EP 1,731,512) or can be made by methods known to a person skilled in the art.

14) A compound of formula (I) where $A^1$, $A^2$, $A^3$, $A^4$, $R^1$, $R^2$, $R^3$ and $R^4$ are as defined for a compound of formula (I) and G is oxygen, can be made by reacting a carboxylic acid of formula (III) or an acid halide of formula (III') where $A^1$, $A^2$, $A^3$, $A^4$, $R^3$ and $R^4$ are as defined for a compound of formula (I), G is oxygen and R is Br, Cl or F (which can be obtained from a compound of the formula (XI) where $A^1$, $A^2$, $A^3$, $A^4$, $R^1$, $R^2$, $R^3$ and $R^4$ are as defined for a compound of formula (I), G is oxygen and R is $C_1$-$C_6$alkoxy), with an amine of formula $HNR^1R^2$ where $R^1$ and $R^2$ are as defined for a compound of formula (I) under conditions described under 8).

Scheme 2a

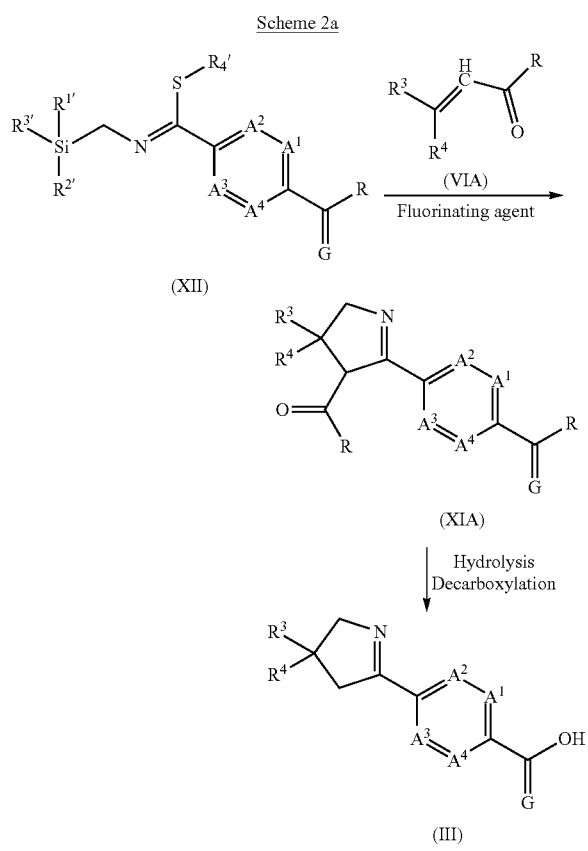

14a) Alternatively a compound of formula (III) where $A^1$, $A^2$, $A^3$, $A^4$, $R^3$ and $R^4$ are as defined for a compound of formula (I) and G is Oxygen can be made by treatment of a compound of formula (XIA) where $A^1$, $A^2$, $A^3$, $A^4$, $R^3$ and $R^4$ are as defined for a compound of formula (I) and R is $C_1$-$C_6$alkoxy under hydrolytic conditions followed by decarboxylation. Such conditions are, for example, treatment with an alkali hydroxide, such as sodium hydroxide or potassium hydroxide, in a solvent, such as ethanol or tetrahydrofuran, in the presence of water. Another alternative is the treatment of the ester with an acid, such as trifluoroacetic acid, in a solvent, such as dichloromethane, followed by addition of water. The reaction is carried out preferably at a temperature of from −20° C. to +100° C., more preferably from 20° C. to 80° C., in particular at 50° C.

14b) A compound of formula (XIA) where $A^1$, $A^2$, $A^3$, $A^4$, $R^3$ and $R^4$ are as defined for a compound of formula (I) and R is $C_1$-$C_6$alkoxy, can be made reacting a compound of formula (XII) where $A^1$, $A^2$, $A^3$, $A^4$ are as defined for a compound of formula (I) R is $C_1$-$C_6$alkoxy, $R^{1'}$, $R^{2'}$ and $R^{3'}$ represent optionally substituted alkyl or optionally substituted phenyl, $R^{4'}$ represents optionally substituted alkyl and G is oxygen with a vinyl compound of formula (VIA) where $R^3$ and $R^4$ are as defined for a compound of formula (I) and R is $C_1$-$C_6$alkoxy, in the presence of a fluorine reagent such as potassium fluoride or tetrabutylammonium fluoride, in a solvent, for example THF. The reaction is carried out preferably at a temperature of from −20° C. to +500° C., more preferably from 0° C. to 100° C., in particular at ambient temperature. Vinyl compounds of formula (VIA) are known from the literature (for example, from J. Org. Chem. (2003), 68(15), 5925-5929) or can be made by methods known to a person skilled in the art.

Scheme 3

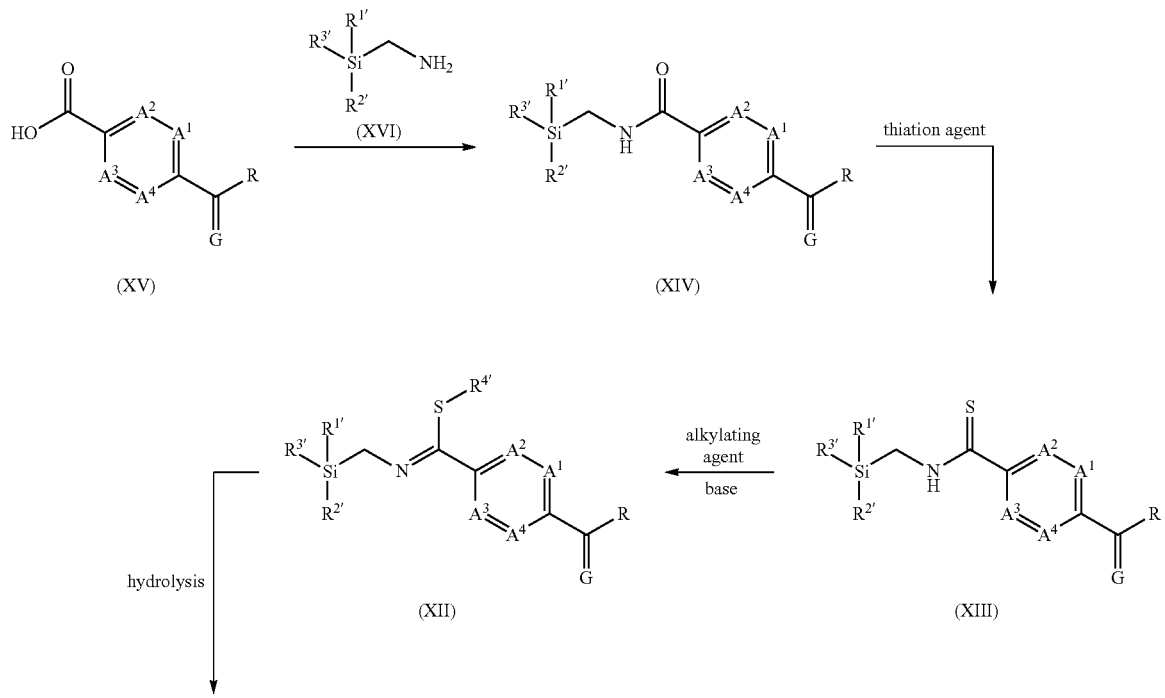

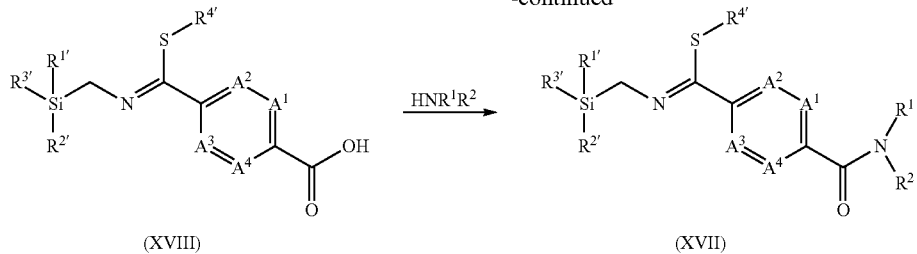

(XVIII) → (XVII)

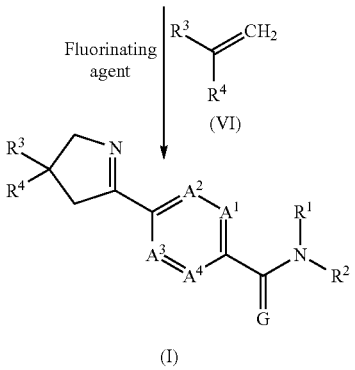

(I)

15) Carboxylic acids of formula (XVIII) where $A^1$, $A^2$, $A^3$, $A^4$ are as defined for a compound of formula (I), $R^{1'}$, $R^{2'}$ and $R^{3'}$ represent optionally substituted alkyl or optionally substituted phenyl, $R^{4'}$ represents optionally substituted alkyl and G is oxygen may be formed from esters of formula (XII), wherein R is $C_1$-$C_6$alkoxy. It is known to a person skilled in the art that there are many methods for the hydrolysis of such esters depending on the nature of the alkoxy group. One widely used method to achieve such a transformation is the treatment of the ester with an alkali hydroxide, such as sodium hydroxide or lithium hydroxide, in a solvent, such as ethanol or tetrahydrofuran, in the presence of water. Another is the treatment of the ester with an acid, such as trifluoroacetic acid, in a solvent, such as dichloromethane, followed by addition of water. The reaction is carried out at temperatures of from 0° C. to 150° C., preferably from 15° C. to 100° C., in particular at 50° C.

16) A compound of formula (XVII) where $A^1$, $A^2$, $A^3$, $A^4$ are as defined for a compound of formula (I), $R^{1'}$, $R^{2'}$ and $R^{3'}$ represent optionally substituted alkyl or optionally substituted phenyl, $R^{4'}$ represents optionally substituted alkyl and G is oxygen may be formed by reaction of acids of formula (XVIII) where $A^1$, $A^2$, $A^3$, $A^4$ are as defined for a compound of formula (I), $R^{1'}$, $R^{2'}$ and $R^{3'}$ represent optionally substituted alkyl or optionally substituted phenyl, $R^{4'}$ represents optionally substituted alkyl and G is oxygen with an amine of formula $HNR^1R^2$ where $R^1$ and $R^2$ are as defined for a compound of formula (I) under conditions described under 8).

17) A compound of formula (I) where $A^1$, $A^2$, $A^3$, $A^4$, $R^1$, $R^2$, $R^3$ and $R^4$ are as defined for a compound of formula (I) and G is oxygen, can be made by reacting a compound of the formula (XVII) where $A^1$, $A^2$, $A^3$, $A^4$, $R^{1'}$, $R^{2'}$, $R^{3'}$ and $R^{4'}$ are as defined for a compound of formula (I), G is oxygen, $R^{1'}$, $R^{2'}$ and $R^{3'}$ represent optionally substituted alkyl or optionally substituted phenyl and $R^{4'}$ represents optionally substituted alkyl with a vinyl compound of formula (VI) where $R^3$ and $R^4$ are as defined for a compound of formula (I), in the presence of a fluorine reagent such as potassium fluoride or tetrabutylammonium fluoride, in a solvent, for example THF under conditions described under 13).

Scheme 3a

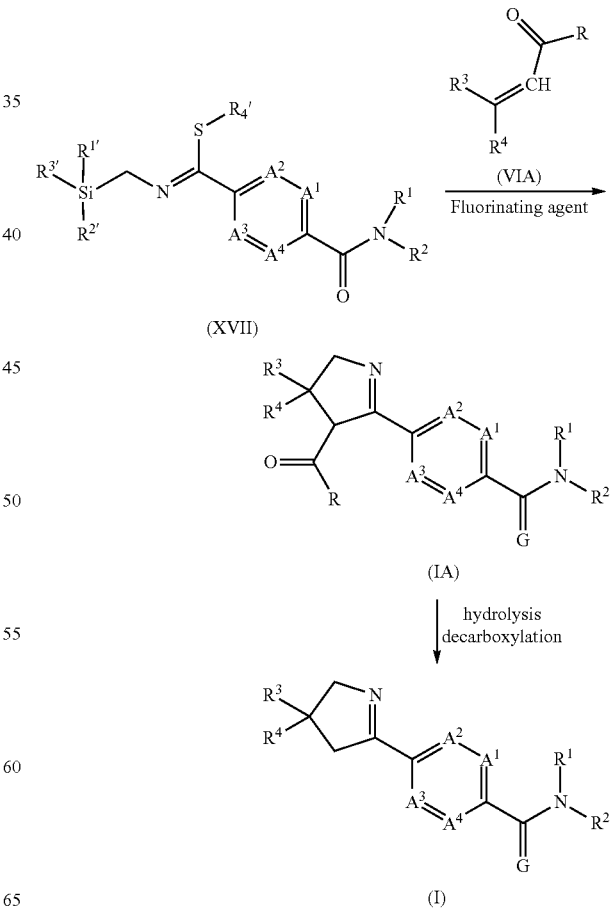

17a) Alternatively a compound of formula (I) where $A^1$, $A^2$, $A^3$, $A^4$, $R^3$ and $R^4$ are as defined herein and G is oxygen can be made by treatment of a compound of formula (IA) where $A^1$, $A^2$, $A^3$, $A^4$, $R^3$ and $R^4$ are as defined for a compound of formula (I), G is oxygen, and R is $C_1$-$C_6$alkoxy, under hydrolytic conditions followed by decarboxylation. Such conditions are, for example, treatment with an alkali hydroxide, such as sodium hydroxide or potassium hydroxide, in a solvent, such as ethanol or tetrahydrofuran, in the presence of water. Another alternative is the treatment of the ester with an acid, such as trifluoroacetic acid, in a solvent, such as dichloromethane, followed by addition of water. The reaction is carried out preferably at a temperature of from −20° C. to +100° C., more preferably from 20° C. to 80° C., in particular at 50° C.

17b) A compound of formula (IA) where $A^1$, $A^2$, $A^3$, $A^4$, $R^3$ and $R^4$ are as defined for a compound of formula (I), G is oxygen, and R is $C_1$-$C_6$alkoxy, can be made reacting a compound of formula (XVII) where $A^1$, $A^2$, $A^3$, $A^4$ are as defined for a compound of formula (I), $R^{1'}$, $R^{2'}$ and $R^{3'}$ represent optionally substituted alkyl or optionally substituted phenyl, $R^{4'}$ represents optionally substituted alkyl and G is oxygen with a vinyl compound of formula (VIA) where $R^3$ and $R^4$ are as defined for a compound of formula (I) and R is $C_1$-$C_6$alkoxy, in the presence of a fluorine reagent such as potassium fluoride or tetrabutylammonium fluoride, in a solvent, for example THF. The reaction is carried out preferably at a temperature of from −20° C. to +500° C., more preferably from 0° C. to 100° C., in particular at ambient temperature. Vinyl compounds of formula (VIA) are known from the literature (for example, from J. Org. Chem. (2003), 68(15), 5925-5929) or can be made by methods known to a person skilled in the art.

18) A compound of formula (I) where $A^1$, $A^2$, $A^3$, $A^4$, $R^1$, $R^2$, $R^3$ and $R^4$ are as defined herein and G is oxygen, can be made by reacting a compound of the formula (XX) where $A^1$, $A^2$, $A^3$, $A^4$, $R^1$, $R^2$, $R^3$ and $R^4$ are as defined for a compound of formula (I) and G is oxygen, with a reducing agent such as Zn/HCl, in a solvent, for example water or DMF or mixtures thereof. The reaction is carried out preferably at a temperature of from −20° C. to +500° C., more preferably from 0° C. to 100° C., in particular at 80° C.

19) A compound of formula (XX) where $A^1$, $A^2$, $A^3$, $A^4$, $R^1$, $R^2$, $R^3$ and $R^4$ are as defined for a compound of formula (I) and G is oxygen, can be made by reacting a compound of the formula (XXI) where $A^1$, $A^2$, $A^3$, $A^4$, $R^1$, $R^2$, $R^3$ and $R^4$ are as defined for a compound of formula (I) and G is oxygen (which may be prepared according to the methods described in WO 2009/080250) with nitromethane in the presence of a base such as NaOH, in a solvent, for example water or DMF or mixtures thereof. The reaction is carried out preferably at a temperature of from −20° C. to +500° C., more preferably from 0° C. to 100° C., in particular at ambient temperature.

20) Alternatively, a compound of formula (I) where $A^1$, $A^2$, $A^3$, $A^4$, $R^1$, $R^2$, $R^3$ and $R^4$ are as defined herein and G is oxygen, as shown in Scheme 4 can be prepared from a compound of the formula (XX) where $A^1$, $A^2$, $A^3$, $A^4$, $R^1$, $R^2$, $R^3$ and $R^4$ are as defined for a compound of formula (I) and G is oxygen via an intermediate (XIX) where $A^1$, $A^2$, $A^3$, $A^4$, $R^1$, $R^2$, $R^3$ and $R^4$ are as defined for a compound of formula (I) and G is oxygen, for example under reaction conditions described under 18).

Representative experimental conditions for this transformation are also described in Tetrahedron Letters 2003, 44, 3701-3703.

Scheme 4

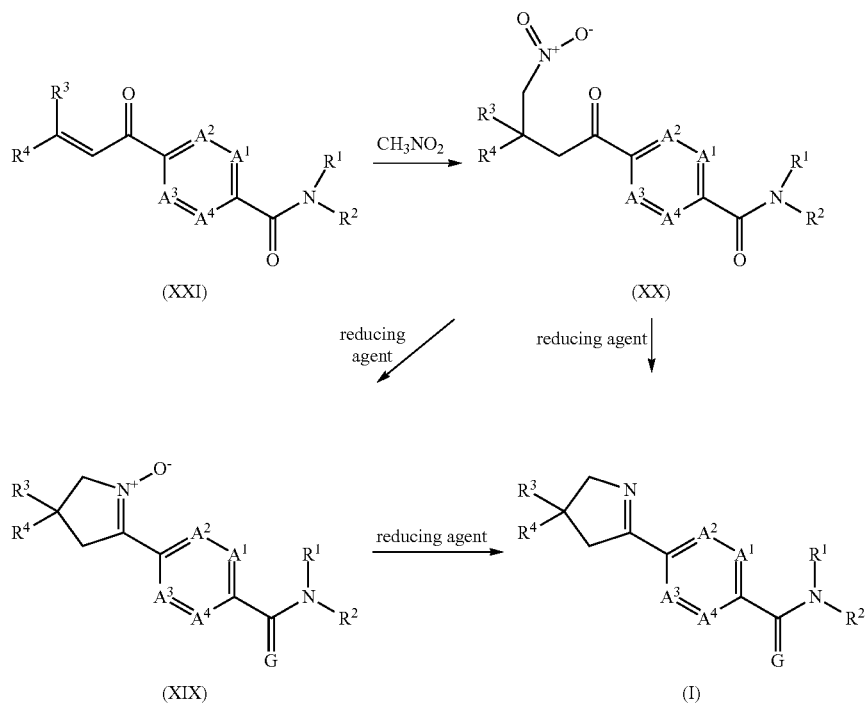

Scheme 5

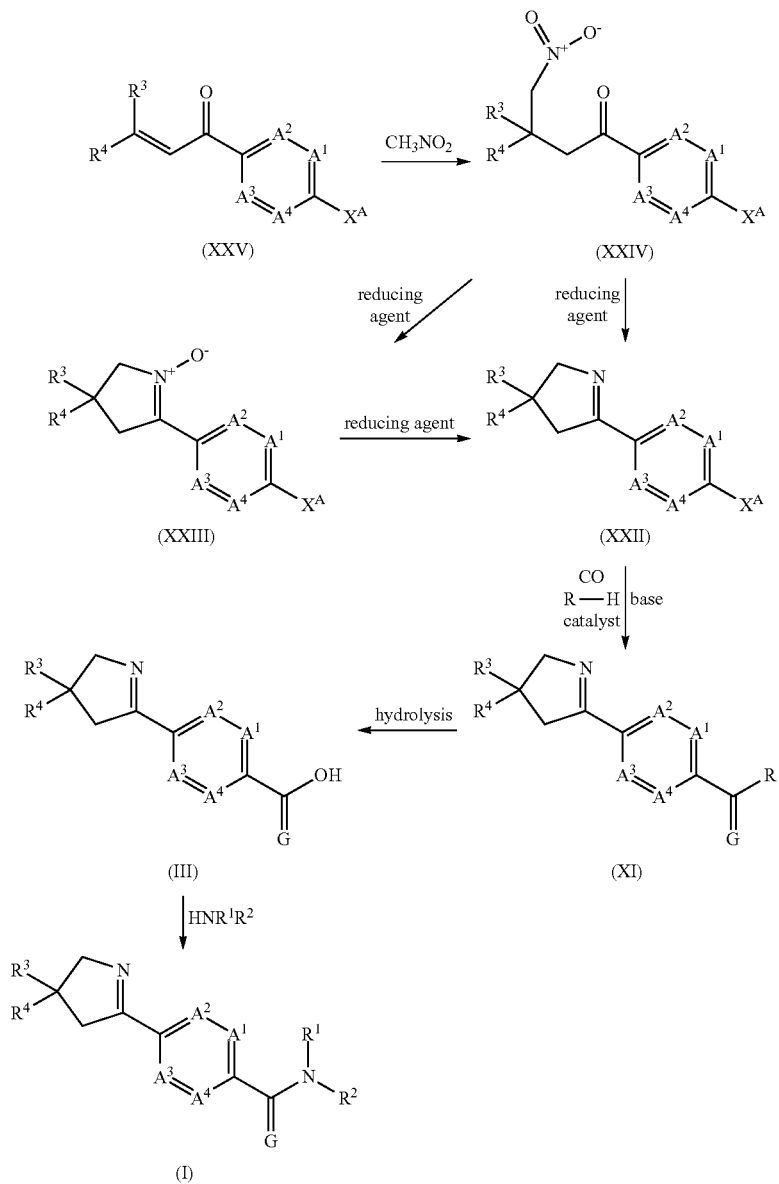

21) A compound of formula (III) where $A^1, A^2, A^3, A^4, R^3$ and $R^4$ are as defined for a compound of formula (I), G is oxygen can be made from an compound of the formula (XI) where $A^1, A^2, A^3, A^4, R^3$ and $R^4$ are as defined for a compound of formula (I), G is oxygen and R is $C_1$-$C_6$alkoxy under conditions described under 6) 22) A compound of formula (XI) where $A^1, A^2, A^3, A^4, R^3$ and $R^4$ are as defined for a compound of formula (I), G is oxygen and R is $C_1$-$C_6$alkoxy can be made by reacting a compound of formula (XXII) where $A^1, A^2, A^3, A^4, R^1, R^2, R^3$ and $R^4$ are as defined for a compound of formula (I) and $X^A$ is a leaving group, for example a halogen atom, such as a bromine atom and G is oxygen as described under 5).

23) A compound of formula (XXII) where $A^1, A^2, A^3, A^4, R^3$ and $R^4$ are as defined for a compound of formula (I) and $X^A$ is a leaving group, for example a halogen atom, such as a bromine atom, can be made by reacting a compound of the formula (XXIV) where $A^1, A^2, A^3, A^4, R^3$ and $R^4$ are as defined for a compound of formula (I) and $X^A$ is a leaving group, such as a bromine atom and G is oxygen under conditions as described under 18).

24) Alternatively, compounds of formula (XXII) where $A^1, A^2, A^3, A^4, R^3$ and $R^4$ are as defined for a compound of formula (I) and $X^A$ is a leaving group, for example a halogen atom, such as a bromine atom and G is oxygen, as shown in Scheme 5 can be prepared from a compound of the formula (XXIV) where $A^1, A^2, A^3, A^4, R^3$ and $R^4$ are as defined for a compound of formula (I) and $X^A$ is a leaving group, for example a halogen atom, such as a bromine atom and G is oxygen via an intermediate (XIII) where $A^1, A^2, A^3, A^4, R^3$ and $R^4$ are as defined for a compound of formula (I) and $X^A$ is a leaving group, for example a halogen atom, such as a bromine atom and G is oxygen for example under reaction conditions described under 18).

25) A compound of formula (XXIV) where $A^1$, $A^2$, $A^3$, $A^4$, $R^3$ and $R^4$ are as defined for a compound of formula (I) and $X^A$ is a leaving group, for example a halogen atom, such as a bromine atom and G is oxygen, can be made by reacting a compound of the formula (XXV) where $A^1$, $A^2$, $A^3$, $A^4$, $R^3$ and $R^4$ are as defined for a compound of formula (I) and $X^A$ is a leaving group, for example a halogen atom, such as a bromine atom and G is oxygen (which may be prepared according to the methods described in WO 2009/080250) under conditions as described under 19).

nide, acetone cyanohydrin, or diethylaluminium cyanide, in a solvent, for example toluene, tetrahydrofuran, acetone, acetic acid, ethanol, or water or mixtures thereof. The reaction is carried out preferably at a temperature of from −20° C. to +500° C., more preferably from 0° C. to 100° C., in particular at ambient temperature. Representative experimental conditions for this transformation are described in Tetrahedron, 64(17), 3642-3654; 2008.

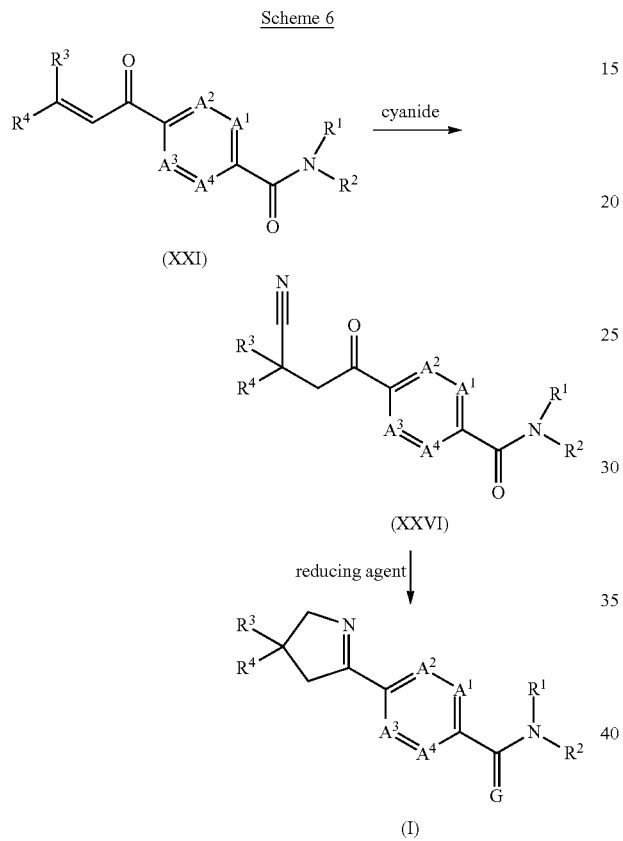

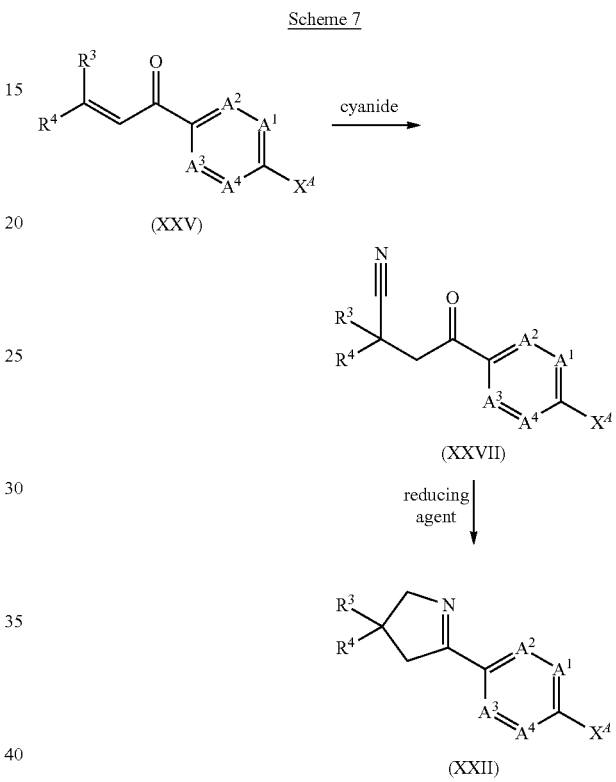

26) Alternatively, a compound of formula (I) where $A^1$, $A^2$, $A^3$, $A^4$, $R^1$, $R^2$, $R^3$ and $R^4$ are as defined for a compound of formula (I) and G is oxygen, can be made by reacting a compound of the formula (XXVI) where $A^1$, $A^2$, $A^3$, $A^4$, $R^1$, $R^2$, $R^3$ and $R^4$ are as defined for a compound of formula (I) and G is oxygen, with a reducing agent such as Raney Ni/$H_2$, in a solvent, for example methanol or ethanol. The reaction is carried out preferably at a temperature of from −20° C. to +500° C., more preferably from 0° C. to 100° C. Representative experimental conditions for this transformation are described by Allen, C. F. H. and Wilson, C. V. in Org Synth. (1947), 27.

27) A compound of formula (XXVI) where $A^1$, $A^2$, $A^3$, $A^4$, $R^1$, $R^2$, $R^3$ and $R^4$ are as defined for a compound of formula (I) and G is oxygen, can be made by reacting a compound of the formula (XXI) where $A^1$, $A^2$, $A^3$, $A^4$, $R^1$, $R^2$, $R^3$ and $R^4$ are as defined for a compound of formula (I) and G is oxygen (which may be prepared according to the methods described in WO 2009/080250) with a cyanide source such as sodium cyanide, potassium cyanide, trimethylsilyl cya- 28) A compound of formula (XXII) where $A^1$, $A^2$, $A^3$, $A^4$, $R^3$ and $R^4$ are as defined for a compound of formula (I) and $X^A$ is a leaving group, for example a halogen atom, such as a bromine atom and G is oxygen, can be made by reacting a compound of the formula (XXVII) where $A^1$, $A^2$, $A^3$, $A^4$, $R^3$ and $R^4$ are as defined for a compound of formula (I) and $X^A$ is a leaving group, for example a halogen atom, such as a bromine atom and G is oxygen (which may be prepared according to the methods described in WO 2009/080250) under conditions as described under 26).

29) A compound of formula (XXVII) where $A^1$, $A^2$, $A^3$, $A^4$, $R^3$ and $R^4$ are as defined for a compound of formula (I) and $X^A$ is a leaving group, for example a halogen atom, such as a bromine atom and G is oxygen, can be made by reacting a compound of the formula (XXV) where $A^1$, $A^2$, $A^3$, $A^4$, $R^3$ and $R^4$ are as defined for a compound of formula (I) and $X^A$ is a leaving group, for example a halogen atom, such as a bromine atom and G is oxygen under conditions as described under 27).

Compounds of formula (I) contain a chiral centre giving rise to enantiomers of the formula (I*) and (I**).

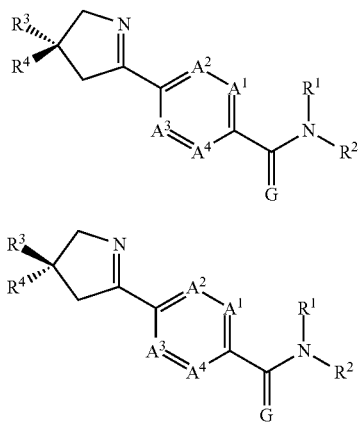

Enantiomerically enriched mixtures of compounds of formula (I*) or (I**) may be prepared, for example, according to schemes 4 or 5 by formation of intermediate XX or XXIV via an asymmetric Michael addition, see for example J. Org. Chem. 2008, 73, 3475-3480 and references cited therein". Alternatively, such enantiomerically enriched mixtures may be prepared according to schemes 6 or 7 by stereoselective addition of cyanide, see for example J. Am. Chem. Soc. 2008, 130, 6072-6073.

A compound of formula (I) may be a mixture of compounds I* and I in any ratio e.g. in a molar ratio of 1:99 to 99:1, e.g. 10:1 to 1:10, e.g. a substantially 50:50 molar ratio. For example, in an enantiomerically enriched mixture of formula I, the molar proportion of compound I** compared to the total amount of both enantiomers is for example greater than 50%, e.g. at least 55, 60, 65, 70, 75, 80, 85, 90, 95, 96, 97, 98, or at least 99%. Likewise, in an enantiomerically enriched mixture of formula I*, the molar proportion of the compound of formula I* compared to the total amount of both enantiomers is for example greater than 50%, e.g. at least 55, 60, 65, 70, 75, 80, 85, 90, 95, 96, 97, 98, or at least 99%.

The compounds of formula (I) can be used to control infestations of insect pests such as Lepidoptera, Diptera, Hemiptera, Thysanoptera, Orthoptera, Dictyoptera, Coleoptera, Siphonaptera, Hymenoptera and Isoptera and also other invertebrate pests, for example, acarine, nematode and mollusc pests. Insects, acarines, nematodes and molluscs are hereinafter collectively referred to as pests. The pests which may be controlled by the use of the invention compounds include those pests associated with agriculture (which term includes the growing of crops for food and fiber products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies).

The compounds of the invention may be used for example on turf, ornamentals, such as flowers, shrubs, broad-leaved trees or evergreens, for example conifers, as well as for tree injection, pest management and the like.

Examples of pest species which may be controlled by the compounds of formula (I) include: *Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. *(thrips)*, *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta migratoria* (locust), *Chortiocetes terminifera* (locust), *Diabrotica* spp. (rootworms), *Panonychus ulmi* (European red mite), *Panonychus citri* (citrus red mite), *Tetranychus urticae* (two-spotted spider mite), *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides felis* (cat flea), *Liriomyza* spp. (leafminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the Mastotermitidae (for example *Mastotermes* spp.), the Kalotermitidae (for example *Neotermes* spp.), the Rhinotermitidae (for example *Coptotermes formosanus, Reticulitermes flavipes, R. speratu*, R. virginicus, R. hesperus, and *R. santonensis*) and the Termitidae (for example *Globitermes sulfureus*), *Solenopsis geminata* (fire ant), *Monomorium pharaonis* (pharaoh's ant), *Damalinia* spp. and *Linognathus* spp. (biting and sucking lice), *Meloidogyne* spp. (root knot nematodes), *Globodera* spp. and *Heterodera* spp. (cyst nematodes), *Pratylenchus* spp. (lesion nematodes), *Rhodopholus* spp. (banana burrowing nematodes), *Tylenchulus* spp. (citrus nematodes), *Haemonchus contortus* (barber pole worm), *Caenorhabditis elegans* (vinegar eelworm), *Trichostrongylus* spp. (gastro intestinal nematodes) and *Deroceras reticulatum* (slug).

The invention therefore provides a method of controlling insects, acarines, nematodes or molluscs which comprises applying an insecticidally, acaricidally, nematicidally or molluscicidally effective amount of a compound of formula (I), or a composition containing a compound of formula (I), to a pest, a locus of pest, preferably a plant, or to a plant susceptible to attack by a pest. The compounds of formula (I) are preferably used against insects or acarines. The compounds of the invention may also be used for controlling insects that are resistant to known insecticides.

The term "plant" as used herein includes seedlings, bushes and trees.

Crops are to be understood as also including those crops which have been rendered tolerant to herbicides or classes of herbicides (e.g. ALS-, GS-, EPSPS-, PPO- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®.

Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood as being those which are obtained by conventional methods of breeding or genetic engineering and contain so-called output traits (e.g. improved storage stability, higher nutritional value and improved flavor).

In order to apply a compound of formula (I) as an insecticide, acaricide, nematicide or molluscicide to a pest, a locus of pest, or to a plant susceptible to attack by a pest, a compound of formula (I) is usually formulated into a composition which includes, in addition to the compound of formula (I), a suitable inert diluent or carrier and, optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (I). The composition is generally used for the control of pests such that a compound of formula (I) is applied at a rate of from 0.1 g to 10 kg per hectare, preferably from 1 g to 6 kg per hectare, more preferably from 1 g to 1 kg per hectare.

When used in a seed dressing, a compound of formula (I) is used at a rate of 0.0001 g to 10 g (for example 0.001 g or 0.05 g), preferably 0.005 g to 10 g, more preferably 0.005 g to 4 g, per kilogram of seed.

In another aspect the present invention provides an insecticidal, acaricidal, nematicidal or molluscicidal composition comprising an insecticidally, acaricidally, nematicidally or molluscicidally effective amount of a compound of formula (I) and for example a suitable carrier or diluent therefor. The composition is preferably an insecticidal or acaricidal composition.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), microemulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (I).

Dustable powders (DP) may be prepared by mixing a compound of formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulfur, lime, flours, talc and other organic and inorganic solid carriers) and mechanically grinding the mixture to a fine powder.

Soluble powders (SP) may be prepared by mixing a compound of formula (I) with one or more water-soluble inorganic salts (such as sodium bicarbonate, sodium carbonate or magnesium sulfate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (I) and one or more powdered solid diluents or carriers, or from pre-formed blank granules by absorbing a compound of formula (I) (or a solution thereof, in a suitable agent) in a porous granular material (such as pumice, attapulgite clays, fuller's earth, kieselguhr, diatomaceous earths or ground corn cobs) or by adsorbing a compound of formula (I) (or a solution thereof, in a suitable agent) on to a hard core material (such as sands, silicates, mineral carbonates, sulfates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (I) in water or an organic solvent, such as a ketone, alcohol or glycol ether. These solutions may contain a surface active agent (for example to improve water dilution or prevent crystallization in a spray tank).

Emulsifiable concentrates (EC) or oil-in-water emulsions (EW) may be prepared by dissolving a compound of formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (I) either as a liquid (if it is not a liquid at room temperature, it may be melted at a reasonable temperature, typically below 70° C.) or in solution (by dissolving it in an appropriate solvent) and then emulsifiying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of formula (I) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (I). SCs may be prepared by ball or bead milling the solid compound of formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (I) may be dry milled and added to water, containing agents hereinbefore described, to produce the desired end product.

Aerosol formulations comprise a compound of formula (I) and a suitable propellant (for example n-butane). A compound of formula (I) may also be dissolved or dispersed in a suitable medium (for example water or a water miscible liquid, such as n-propanol) to provide compositions for use in non-pressurized, hand-actuated spray pumps.

A compound of formula (I) may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerization stage such that an aqueous dispersion of oil droplets is obtained, in which each oil droplet is encapsulated by a polymeric shell and contains a compound of formula (I) and, optionally, a carrier or diluent therefor. The polymeric shell may be produced by either an interfacial polycondensation reaction or by a coacervation procedure. The compositions may provide for controlled release of the compound of formula (I) and they may be used for seed treatment. A compound of formula (I) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (I)). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (I)).

A compound of formula (I) may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be surface SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulfuric acid (for example sodium lauryl sulfate), salts of sulfonated aromatic compounds (for example sodium dodecylbenzenesulfonate, calcium dodecylbenzenesulfonate, butylnaphthalene sulfonate and mixtures of sodium di-isopropyl- and tri-isopropyl-naphthalene sulfonates), ether sulfates, alcohol ether sulfates (for example sodium laureth-3-sulfate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulfosuccinamates, paraffin or olefine sulfonates, taurates and lignosulfonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octyl-cresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (I) may be applied by any of the known means of applying pesticidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapor or applied through distribution or incorporation of a composition (such as a granular composition or a composition packed in a water-soluble bag) in soil or an aqueous environment.

A compound of formula (I) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs, SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (I) (for example 0.0001 to 10%, by weight) depending upon the purpose for which they are to be used.

A compound of formula (I) may be used in mixtures with fertilizers (for example nitrogen-, potassium- or phosphorus-containing fertilizers). Suitable formulation types include granules of fertilizer. The mixtures preferably contain up to 25% by weight of the compound of formula (I).

The invention therefore also provides a fertilizer composition comprising a fertilizer and a compound of formula (I).

The compositions of this invention may contain other compounds having biological activity, for example micronutrients or compounds having fungicidal activity or which possess plant growth regulating, herbicidal, insecticidal, nematicidal or acaricidal activity.

The compound of formula (I) may be the sole active ingredient of the composition or it may be admixed with one or more additional active ingredients such as a pesticide, fungicide, synergist, herbicide or plant growth regulator where appropriate. An additional active ingredient may: provide a composition having a broader spectrum of activity or increased persistence at a locus; synergize the activity or complement the activity (for example by increasing the speed of effect or overcoming repellency) of the compound of formula (I); or help to overcome or prevent the development of resistance to individual components. The particular additional active ingredient will depend upon the intended utility of the composition. Examples of suitable pesticides include the following:

a) Pyrethroids, such as permethrin, cypermethrin, fenvalerate, esfenvalerate, deltamethrin, cyhalothrin (in particular lambda-cyhalothrin, gamma-cyhalothrin), bifenthrin, fenpropathrin, cyfluthrin, tefluthrin, fish safe pyrethroids (for example ethofenprox), natural pyrethrin, tetramethrin, S-bioallethrin, fenfluthrin, prallethrin or 5-benzyl-3-furylmethyl-(E)-(1R,3S)-2,2-dimethyl-3-(2-oxothiolan-3-ylidenemethyl)cyclopropane carboxylate;
b) Organophosphates, such as profenofos, sulprofos, acephate, methyl parathion, azinphos-methyl, demeton-s-methyl, heptenophos, thiometon, fenamiphos, monocrotophos, profenofos, triazophos, methamidophos, dimethoate, phosphamidon, malathion, chlorpyrifos, phosalone, terbufos, fensulfothion, fonofos, phorate, phoxim, pirimiphos-methyl, pirimiphos-ethyl, fenitrothion, fosthiazate or diazinon;
c) Carbamates (including aryl carbamates), such as pirimicarb, triazamate, cloethocarb, carbofuran, furathiocarb, ethiofencarb, aldicarb, thiofurox, carbosulfan, bendiocarb, fenobucarb, propoxur, methomyl or oxamyl;
d) Benzoyl ureas, such as diflubenzuron, triflumuron, hexaflumuron, flufenoxuron or chlorfluazuron;
e) Organic tin compounds, such as cyhexatin, fenbutatin oxide or azocyclotin;
f) Pyrazoles, such as tebufenpyrad and fenpyroximate;
g) Macrolides, such as avermectins or milbemycins, for example abamectin, emamectin benzoate, ivermectin, milbemycin, spinosad, azadirachtin or spinetoram;
h) Hormones or pheromones;
i) Organochlorine compounds, such as endosulfan (in particular alpha-endosulfan), benzene hexachloride, DDT, chlordane or dieldrin;
j) Amidines, such as chlordimeform or amitraz;
k) Fumigant agents, such as chloropicrin, dichloropropane, methyl bromide or metam;
l) Neonicotinoid compounds, such as imidacloprid, thiacloprid, acetamiprid, nitenpyram, dinotefuran, thiamethoxam, clothianidin, nithiazine or flonicamid;
m) Diacylhydrazines, such as tebufenozide, chromafenozide or methoxyfenozide;
n) Diphenyl ethers, such as diofenolan or pyriproxifen;
o) Indoxacarb;
p) Chlorfenapyr;
q) Pymetrozine;
r) Spirotetramat, spirodiclofen or spiromesifen;
s) Diamides, such as flubendiamide, chlorantraniliprole or cyantraniliprole;
t) Sulfoxaflor;
u) Metaflumizone;
v) Fipronil and Ethiprole; or
w) Pyrifluqinazon.

In addition to the major chemical classes of pesticide listed above, other pesticides having particular targets may be employed in the composition, if appropriate for the intended utility of the composition. For instance, selective insecticides for particular crops, for example stemborer specific insecticides (such as cartap) or hopper specific insecticides (such as buprofezin) for use in rice may be employed. Alternatively insecticides or acaricides specific for particular insect species/stages may also be included in the compositions (for example acaricidal ovo-larvicides, such as clofentezine, flubenzimine, hexythiazox or tetradifon; acaricidal motilicides, such as dicofol or propargite; acaricides, such as bromopropylate or chlorobenzilate; or growth regulators, such as hydramethylnon, cyromazine, methoprene, chlorfluazuron or diflubenzuron).

Examples of fungicidal compounds which may be included in the composition of the invention are (E)-N-methyl-2-[2-(2,5-dimethylphenoxymethyl)phenyl]-2-methoxy-iminoacetamide (SSF-129), 4-bromo-2-cyano-N,N-dimethyl-6-trifluoromethyl-benzimidazole-1-sulfonamide, α-[N-(3-chloro-2,6-xylyl)-2-methoxyacetamido]-γ-butyrolactone, 4-chloro-2-cyano-N,N-dimethyl-5-p-tolylimidazole-1-sulfonamide (IKF-916, cyamidazosulfamid), 3-5-dichloro-N-(3-chloro-1-ethyl-1-methyl-2-oxopropyl)-4-methylbenzamide (RH-7281, zoxamide), N-allyl-4,5,-dimethyl-2-trimethylsilylthiophene-3-carboxamide (MON65500), N-(1-cyano-1,2-dimethylpropyl)-2-(2,4-dichlorophenoxy)-propionamide (AC382042), N-(2-methoxy-5-pyridyl)-cyclopropane carboxamide, acibenzolar (CGA245704) (e.g. acibenzolar-S-methyl), alanycarb, aldimorph, anilazine, azaconazole, azoxystrobin, benalaxyl, benomyl, benthiavalicarb, biloxazol, bitertanol, bixafen, blasticidin S, boscalid, bromuconazole, bupirimate, captafol, captan, carbendazim, carbendazim chlorhydrate, carboxin, carpropamid, carvone, CGA41396, CGA41397, chinomethionate, chlorothalonil, chlorozolinate, clozylacon, copper containing compounds such as copper oxychloride, copper oxyquinolate, copper sulfate, copper tallate and Bordeaux mixture, cyclufenamid, cymoxanil, cyproconazole, cyprodinil, debacarb, di-2-pyridyl disulfide 1,1'-dioxide, dichlofluanid, diclomezine, dicloran, diethofencarb, difenoconazole, difenzoquat, diflumetorim, O,O-di-iso-propyl-S-benzyl thiophosphate, dimefluazole, dimetconazole, dimethomorph, dimethirimol, diniconazole, dinocap, dithianon, dodecyl dimethyl ammonium chloride, dodemorph, dodine, doguadine, edifenphos, epoxiconazole, ethirimol, ethyl-(Z)-N-benzyl-N-([methyl(methyl-thioethylideneamino-oxycarbonyl)amino]thio)-β-alaninate, etridiazole, famoxadone, fenamidone (RPA407213), fenarimol, fenbuconazole, fenfuram, fenhexamid (KBR2738), fenpiclonil, fenpropidin, fenpropimorph, fentin acetate, fentin hydroxide, ferbam, ferimzone, fluazinam, fludioxonil, flumetover, fluopyram, fluoxastrobin, fluoroimide, fluquinconazole, flusilazole, flutolanil, flutriafol, fluxapyroxad, folpet, fuberidazole, furalaxyl, furametpyr, guazatine, hexaconazole, hydroxyisoxazole, hymexazole, imazalil, imibenconazole, iminoctadine, iminoctadine triacetate, ipconazole, iprobenfos, iprodione, iprovalicarb (SZX0722), isopropanyl butyl carbamate, isoprothiolane, isopyrazam, kasugamycin, kresoxim-methyl, LY186054, LY211795, LY248908, mancozeb, mandipropamid, maneb, mefenoxam, metalaxyl, mepanipyrim, mepronil, metalaxyl, metconazole, metiram, metiram-zinc, metominostrobin, myclobutanil, neoasozin, nickel dimethyldithiocarbamate, nitrothal-isopropyl, nuarimol, ofurace, organomercury compounds, oxadixyl, oxasulfuron, oxolinic acid, oxpoconazole, oxycarboxin, pefurazoate, penconazole, pencycuron, penflufen, penthiopyrad, phenazin oxide, phosetyl-A1, phosphorus acids, phthalide, picoxystrobin (ZA1963), polyoxinD, polyram, probenazole, prochloraz, procymidone, propamocarb, propiconazole, propineb, propionic acid, prothioconazole, pyrazophos, pyrifenox, pyrimethanil, pyraclostrobin, pyroquilon, pyroxyfur, pyrrolnitrin, quaternary ammonium compounds, quinomethionate, quinoxyfen, quintozene, sedaxane, sipconazole (F-155), sodium pentachlorophenate, spiroxamine, streptomycin, sulfur, tebuconazole, tecloftalam, tecnazene, tetraconazole, thiabendazole, thifluzamid, 2-(thiocyanomethylthio)benzothiazole, thiophanate-methyl, thiram, timibenconazole, tolclofos-methyl, tolylfluanid, triadimefon, triadimenol, triazbutil, triazoxide, tricyclazole, tridemorph, trifloxystrobin (CGA279202), triforine, triflumizole, triticonazole, validamycin A, vapam, vinclozolin, zineb and ziram, a compound of formula (A), a compound of formula (B) and a compound of formula (C)

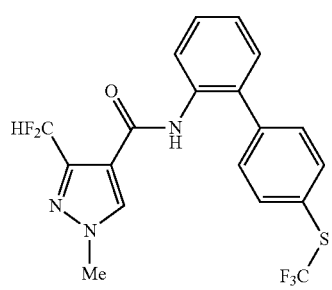

(A)

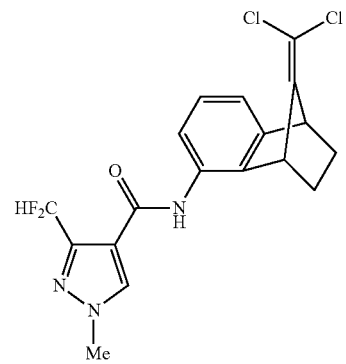

(B)

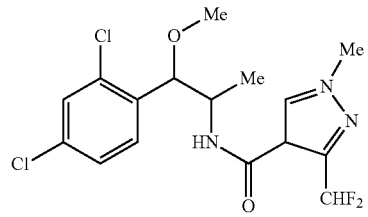

(C)

The compounds of formula (I) may be mixed with soil, peat or other rooting media for the protection of plants against seed-borne, soil-borne or foliar fungal diseases.

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which may be included is propanil. An example of a plant growth regulator for use in cotton is PIX™.

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The following Examples illustrate, but do not limit, the invention.

PREPARATION EXAMPLES

The following abbreviations were used in this section: s=singlet; bs=broad singlet; d=doublet; dd=double doublet; dt=double triplet; t=triplet, tt=triple triplet, q=quartet, sept=septet; m=multiplet; Me=methyl; Et=ethyl; Pr=propyl; Bu=butyl; M.p.=melting point; RT=retention time, [M+H]$^+$=molecular mass of the molecular cation, [M−H]$^-$=molecular mass of the molecular anion.

The following LC-MS methods were used to characterize the compounds:

Method A

| | |
|---|---|
| MS | ZQ Mass Spectrometer from Waters (single quadrupole mass spectrometer), ionization method: electrospray, polarity: positive ionization, capillary (kV) 3.00, cone (V) 30.00, source temperature (° C.) 100, desolvation temperature (° C.) 250, cone gas flow (L/Hr) 50, desolvation gas flow (L/Hr) 400, mass range: 150 to 1000 Da. |
| LC | HP 1100 HPLC from Agilent: solvent degasser, quaternary pump, heated column compartment and diode-array detector.<br>Column: Phenomenex Gemini C18, length (mm) 30, internal diameter (mm) 3, particle size (μm) 3, temperature (° C.) 60, DAD wavelength range (nm): 200 to 500, solvent gradient: A = 0.05% v/v formic acid in water and B = 0.04% v/v formic acid in acetonitrile/methanol (4:1). |

| Time (min) | A % | B % | Flow (ml/min) |
|---|---|---|---|
| 0.0 | 95 | 5.0 | 1.7 |
| 2.0 | 0.0 | 100 | 1.7 |
| 2.8 | 0.0 | 100 | 1.7 |
| 2.9 | 95 | 5.0 | 1.7 |

Method B

| | |
|---|---|
| MS | ZMD Mass Spectrometer from Waters (single quadrupole mass spectrometer), ionization method: electrospray, polarity: positive ionization, capillary (kV) 3.00, cone (V) 30.00, extractor (V) 3.00, source temperature (° C.) 150, desolvation temperature (° C.) 320, cone gas flow (L/Hr) 50, desolvation gas flow (L/Hr) 400, mass range: 150 to 800 Da. |
| LC | Alliance 2795 LC HPLC from Waters: quaternary pump, heated column compartment and diode-array detector.<br>Column: Waters Atlantis dc18, length (mm) 20, internal diameter (mm) 3, particle size (μm) 3, temperature (° C.) 40, DAD wavelength range (nm): 200 to 500, solvent gradient: A = 0.1% v/v formic acid in water and B = 0.1% v/v formic acid in acetonitrile. |

| Time (min) | A % | B % | Flow (ml/min) |
|---|---|---|---|
| 0.0 | 80 | 20 | 1.7 |
| 5.0 | 0.0 | 100 | 1.7 |
| 5.6 | 0.0 | 100 | 1.7 |
| 6.0 | 80 | 20 | 1.7 |

Method C

| | |
|---|---|
| MS | ZQ Mass Spectrometer from Waters (single quadrupole mass spectrometer), ionization method: electrospray, polarity: positive ionization, capillary (kV) 3.00, cone (V) 30.00, extractor (V) 3.00, source temperature (° C.) 100, desolvation temperature (° C.) 200, cone gas flow (L/Hr) 200, desolvation gas flow (L/Hr) 250, mass range: 150 to 800 Da. |
| LC | 1100er Series HPLC from Agilent: quaternary pump, heated column compartment and diode-array detector.<br>Column: Waters Atlantis dc18, length (mm) 20, internal diameter (mm) 3, particle size (μm) 3, temperature (° C.) 40, DAD wavelength range (nm): 200 to 500, solvent gradient: A = 0.1% v/v formic acid in water and B = 0.1% v/v formic acid in acetonitrile. |

| Time (min) | A % | B % | Flow (ml/min) |
|---|---|---|---|
| 0.0 | 90 | 10 | 1.7 |
| 5.5 | 0.0 | 100 | 1.7 |
| 5.8 | 0.0 | 100 | 1.7 |
| 5.9 | 90 | 10 | 1.7 |

Method D

| | |
|---|---|
| MS | ZMD Mass Spectrometer from Waters (single quadrupole mass spectrometer), ionization method: electrospray, polarity: positive ionization, capillary (kV) 3.00, cone (V) 30.00, extractor (V) 3.00, source temperature (° C.) 150, desolvation temperature (° C.) 320, cone gas flow (L/Hr) 50, desolvation gas flow (L/Hr) 400, mass range: 150 to 800 Da. |
| LC | Alliance 2795 LC HPLC from Waters: quaternary pump, heated column compartment and diode-array detector. |

| Time (min) | A % | B % | Flow (ml/min) |
| --- | --- | --- | --- |
| 0.0 | 80 | 20 | 1.7 |
| 2.5 | 0.0 | 100 | 1.7 |
| 2.8 | 0.0 | 100 | 1.7 |
| 2.9 | 80 | 20 | 1.7 |

Method E

| | |
| --- | --- |
| MS | ZQ Mass Spectrometer from Waters (single quadrupole mass spectrometer), ionization method: electrospray, polarity: positive ionization, capillary (kV) 3.00, cone (V) 30.00, extractor (V) 3.00, source temperature (° C.) 100, desolvation temperature (° C.) 200, cone gas flow (L/Hr) 200, desolvation gas flow (L/Hr) 250, mass range: 150 to 800 Da. |
| LC | 1100er Series HPLC from Agilent: quaternary pump, heated column compartment and diode-array detector. Column: Waters Atlantis dc18, length (mm) 20, internal diameter (mm) 3, particle size (μm) 3, temperature (° C.) 40, DAD wavelength range (nm): 200 to 500, solvent gradient: A = 0.1% v/v formic acid in water and B = 0.1% v/v formic acid in acetonitrile. |

| Time (min) | A % | B % | Flow (ml/min) |
| --- | --- | --- | --- |
| 0.0 | 80 | 20 | 1.7 |
| 2.5 | 0.0 | 100 | 1.7 |
| 2.8 | 0.0 | 100 | 1.7 |
| 2.9 | 80 | 20 | 1.7 |

Example I1

Preparation of 4-bromo-3-methyl-benzylamine

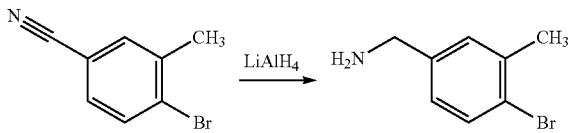

To a solution of 4-bromo-3-methyl-benzonitrile (commercially available) (15 g) in diethyl ether (150 ml) under an argon atmosphere was added a solution of lithium aluminum hydride in diethyl ether (1M) (150 ml) at ambient temperature. The reaction mixture was stirred at 40° C. for 2 hours. Then the reaction mixture was cooled to 0° C. and quenched by successive addition of water (10.5 ml), aqueous sodium hydroxide (20% w/w) (7.5 ml) and water (37.5 ml). The phases were separated. The organic phase was filtered through a plug of silica gel and the filtrate concentrated to give 4-bromo-3-methyl-benzylamine (15.11 g) as a yellow oil. 1H-NMR (400 MHz, CDCl$_3$): 7.47 (d, 1H), 7.19 (s, 1H), 6.98 (d, 1H), 3.80 (s, 2H), 2.39 (s, 3H) ppm.

Example I2

Preparation of N-(4-bromo-3-methyl-benzyl)-formamide

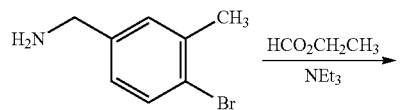

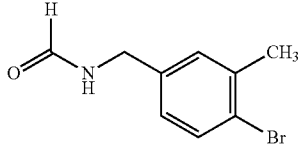

To a solution of 4-bromo-3-methyl-benzylamine (15.11 g) (Example I1) in ethyl formate (150 ml) was added triethylamine (1.5 ml) at ambient temperature. The reaction mixture was stirred at reflux for 16 hours. The reaction mixture was concentrated and the residue was triturated with diisopropyl ether/heptane (1:1) (100 ml) to give N-(4-bromo-3-methyl-benzyl)-formamide (14.04 g) as a white solid. 1H-NMR (400 MHz, CDCl$_3$): 8.28 (s, 1H), 7.49 (m, 1H), 7.16 (s, 1H), 6.97 (m, 1H), 5.85 (s, 1H), 4.42 (m, 2H), 2.39 (s, 3H) ppm.

Example I3

Preparation of 1-bromo-4-isocyanomethyl-2-methyl-benzene

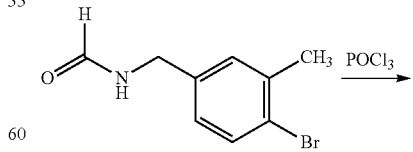

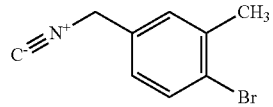

To a solution of N-(4-bromo-3-methyl-benzyl)-formamide (4.3 g) (Example I2) in dichloromethane (70 ml) was added a solution of phosphorus oxychloride (2.8 g) in dichloromethane (15 ml) at 0-5° C. The reaction mixture was stirred at ambient temperature for 16 hours. The reaction mixture was poured onto a mixture of ice and water (400 ml), and sodium hydrogen carbonate (saturated) (100 ml) and ethyl acetate (250 ml) were added. The phases were separated and the organic phase was washed with brine, dried over sodium sulfate and concentrated to give 1-bromo-4-isocyanomethyl-2-methyl-benzene (4.52 g) as a brown oil. 1H-NMR (400 MHz, CDCl$_3$): 7.54 (m, 1H), 7.22 (s, 1H), 7.03 (m, 1H), 4.57 (s, 2H), 2.42 (s, 3H) ppm.

Example I4

Preparation of 2-(4-bromo-3-methyl-phenyl)-4-(3,5-dichloro-phenyl)-4-trifluoromethyl-3,4-dihydro-2H-pyrrole

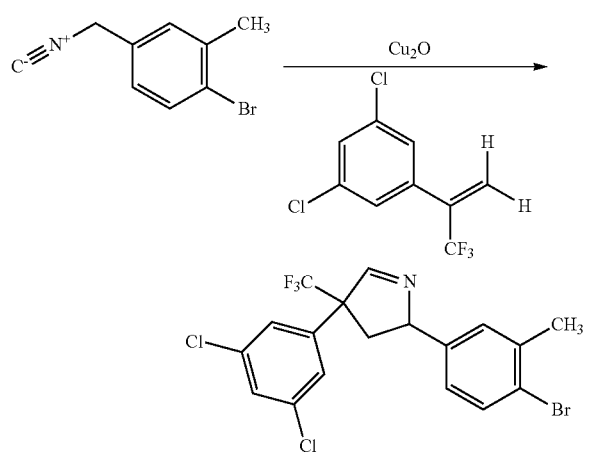

A mixture of 1,3-dichloro-5-(1-trifluoromethyl-vinyl)-benzene (8.03 g) (made as described in EP 1,731,512), 1-bromo-4-isocyanomethyl-2-methyl-benzene (Example I3) (4.16 g) and copper(I) oxide (0.13 g) in toluene (50 ml) was stirred at 110° C. for 16 hours. The reaction mixture was concentrated and the residue purified by chromatography on silica gel (eluent: ethyl acetate/heptane) to give 2-(4-bromo-3-methyl-phenyl)-4-(3,5-dichloro-phenyl)-4-trifluoromethyl-3,4-dihydro-2H-pyrrole (2.39 g). 1H-NMR (400 MHz, CDCl$_3$): 7.39-6.86 (m, 7H), 5.39-4.98 (m, 1H), 3.24-2.77 (m, 1H), 2.35 (m, 3H), 2.32-2.09 (m, 1H) ppm.

Example I5

Preparation of 4-[4-(3,5-dichloro-phenyl)-4-trifluoromethyl-3,4-dihydro-2H-pyrrol-2-yl]-2-methyl-benzoic acid ethyl ester

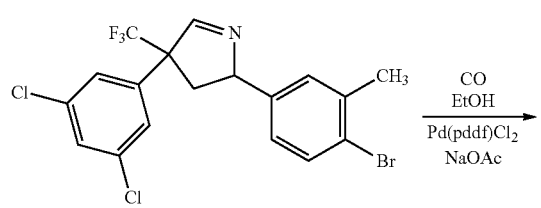

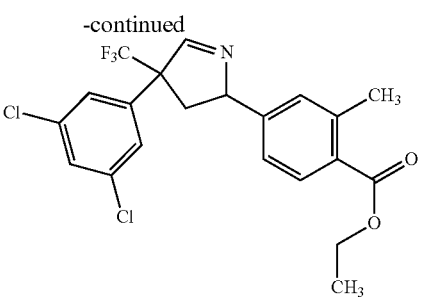

To a solution of 2-(4-bromo-3-methyl-phenyl)-4-(3,5-dichloro-phenyl)-4-trifluoromethyl-3,4-dihydro-2H-pyrrole (Example I4) (7.0 g) in a mixture of ethanol (60 ml) and dimethylformamide (20 ml), was added dichloro 1,1'-bis(diphenylphosphino)ferrocene palladium(II) dichloromethane adduct ("Pd(dppf)Cl$_2$") (0.8 g) and sodium acetate (1.4 g) at ambient temperature. The reaction mixture was stirred in a pressure reactor in an atmosphere of carbon monoxide (6 bar) at 85° C. for 16 hours. The reaction mixture was cooled to ambient temperature, the ethanol was evaporated and aqueous sodium hydrogen carbonate (saturated) (200 ml) and ethyl acetate (250 ml) were added. The phases were separated and the organic phase was dried over sodium sulfate and concentrated. The residue was purified by chromatography on silica gel (eluent: gradient of 0-4% v/v methanol in dichloromethane) to give 4-[4-(3,5-dichloro-phenyl)-4-trifluoromethyl-3,4-dihydro-2H-pyrrol-2-yl]-2-methyl-benzoic acid ethyl ester (2.8 g). 1H-NMR (CDCl$_3$, 400 MHz): 8.04-7.06 (m, 7H), 5.46-5.06 (m, 1H), 4.35 (m, 2H), 3.27-3.79 (m, 1H), 2.59 (m, 3H), 2.38-2.10 (m, 1H), 1.39 (m, 3H) ppm.

Example I6

Preparation of 4-[4-(3,5-dichloro-phenyl)-4-trifluoromethyl-4,5-dihydro-3H-pyrrol-2-yl]-2-methyl-benzoic acid

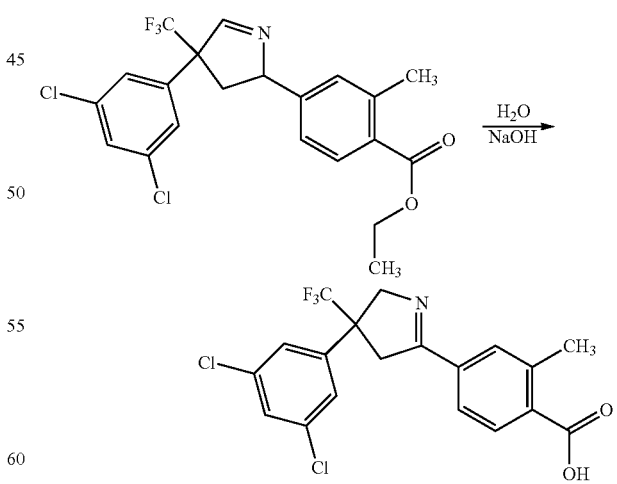

To a solution of 4-[4-(3,5-dichloro-phenyl)-4-trifluoromethyl-3,4-dihydro-2H-pyrrol-2-yl]-2-methyl-benzoic acid ethyl ester (Example I5) (2.8 g) in ethanol (40 ml) was added a solution of sodium hydroxide (0.51 g) in water (15 ml). The reaction mixture was stirred at reflux for 1 hour. After cooling to ambient temperature aqueous hydrochloric acid (1M) (20 ml), water (150 ml) and ethyl acetate (200 ml) was added. The phases were separated and the organic phase was washed with brine, dried over sodium sulfate and concentrated. The residue was recrystallised from diisopropyl ether to give 4-[4-(3,5-dichloro-phenyl)-4-trifluoromethyl-4,5-dihydro-3H-pyrrol-2-yl]-2-methyl-benzoic acid (2.02 g) as a white solid. 1H-NMR (d$_6$-DMSO, 400 MHz): 13.07 (s, 1H), 7.91-7.58 (m, 6H), 4.85 (d, 1H), 4.44 (d, 1H), 3.92-3.35 (m, 2H), 2.58 (s, 3H) ppm.

Example I7

Preparation of 2-methyl-N-trimethylsilanylmethyl-terephthalamic acid methyl ester

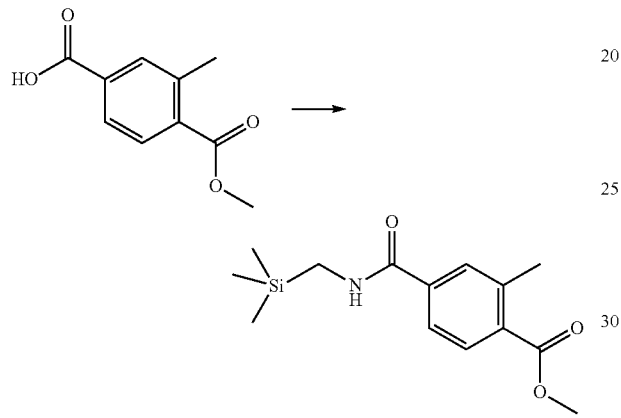

To a solution of 2-methyl-terephthalic acid 1-methylester (preparation see WO 2000/021920) (1.43 g) in dichloromethane (10 ml) was added N-(-3-dimethylaminopropyl)-N'-ethylcarbodiimid hydrochloride (1.84 g), N,N-dimethylaminopyridine (0.41 g) and trimethylsilylmethylamine (1 ml). The reaction mixture was stirred at ambient temperature. for 2 hours. The reaction mixture was concentrated and the residue purified by chromatography on silica gel (eluent: ethyl acetate/heptanes 1:3) to give 2-methyl-N-trimethylsilanylmethyl-terephthalamic acid methyl ester (1.85 g). 1H-NMR (400 MHz, CDCl$_3$): 7.72 (d, 1H), 7.45 (s, 1H), 7.40 (d, 1H), 5.85 (s, 1H), 3.78 (s, 3H), 2.84 (d, 2H), 2.49 (s, 3H), 0.00 (s, 9H) ppm. 2-Methyl-N-trimethylsilanylmethyl-terephthalamic acid tert-butyl ester was obtained using a similar procedure. 1H-NMR (400 MHz, CDCl$_3$): 7.82 (d, 1H), 7.48 (s, 1H), 7.39 (d, 1H), 5.70 (s, 1H), 2.82 (d, 2H), 2.48 (s, 3H), 1.48 (s, 9H), 0.00 (s, 9H) ppm.

Example I8

Preparation of 2-methyl-4-(trimethylsilanylmethyl-thiocarbamoyl)-benzoic acid methyl ester

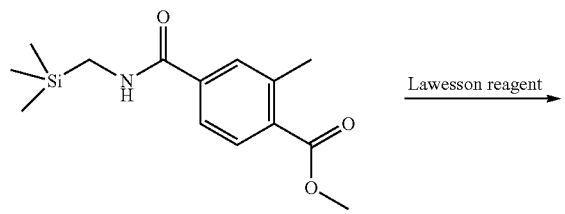

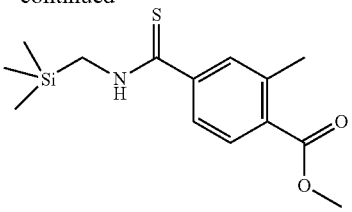

To a solution of 2-methyl-N-trimethylsilanylmethyl-terephthalamic acid methyl ester (Example I7) (1.83 g) in toluene (50 ml) was added 2,4-bis(4-methoxyphenyl)-1,3,2,4-dithiadiphosphetane 2,4-disulfide (Lawesson reagent) (2.65 g). The reaction mixture was stirred at ambient temperature for 30 minutes and then at 110° C. for 1.5 hours. The reaction mixture was concentrated and the residue purified by chromatography on silica gel (eluent: ethyl acetate/heptanes 1:5) to give 2-methyl-4-(trimethylsilanylmethyl-thiocarbamoyl)-benzoic acid methyl ester (1.85 g). 1H-NMR (400 MHz, CDCl$_3$): 7.75-7.20 (m, 3H), 3.70 (s, 3H), 3.35 (m, 2H), 2.45 (s, 3H), 0.00 (s, 9H) ppm.

2-Methyl-4-(trimethylsilanylmethyl-thiocarbamoyl)-benzoic acid tert-butyl ester was obtained using a similar procedure. $^1$H-NMR (400 MHz, CDCl$_3$): 7.62 (d, 1H), 7.40 (s, br, 1H), 7.35 (s, 1H), 7.25 (d, 1H), 3.35 (d, 2H), 2.40 (s, 3H), 1.40 (s, 9H), 0.00 (s, 9H) ppm.

Example I9

Preparation of 2-methyl-4-(methylsulfanyl-trimethylsilanylmethylimino]-methyl)-benzoic acid methyl ester

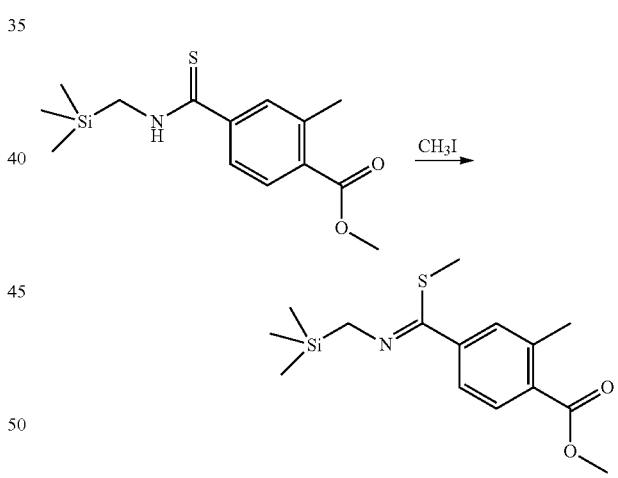

To a solution of 2-methyl-4-(trimethylsilanylmethyl-thiocarbamoyl)-benzoic acid methyl ester (Example I8) (200 mg) in acetonitrile (4 ml) was added potassium carbonate (140 mg) and methyl iodide (120 mg). The reaction mixture was stirred at ambient temperature for 20 hours. Water and ethyl acetate was added to the reaction mixture. The phases were separated and the organic phase was washed with brine, dried over sodium sulfate and concentrated. The residue purified by chromatography on silica gel (eluent: ethyl acetate/heptanes 1:5) to give 2-methyl-4-(methylsulfanyl-trimethylsilanylmethylimino]-methyl)-benzoic acid methyl ester (124 mg). 1H-NMR (400 MHz, CDCl$_3$): 7.82-7.20 (m, 3H), 3.80 (s, 3H), 3.50 (m, 2H), 2.50 (s, 3H), 1.92 (s, 3H), 0.00 (s, 9H) ppm.

2-Methyl-4-{methylsulfanyl-E)-trimethylsilanylmethylimino]-methyl}-benzoic acid tert-butyl ester was obtained using a similar procedure. 1H-NMR (400 MHz, CDCl₃): 7.62 (d, 1H), 7.23-7.20 (m, 2H), 3.03 (m, 2H), 2.48 (s, 3H), 1.95 (s, 3H), 1.45 (s, 9H), 0.00 (s, 9H) ppm.

Example I10

Preparation of 4-[4-(3,5-Bis-trifluoromethyl-phenyl)-4-trifluoromethyl-3,4-dihydro-2H-pyrrol-2-yl]-2-methyl-benzoic acid methyl ester

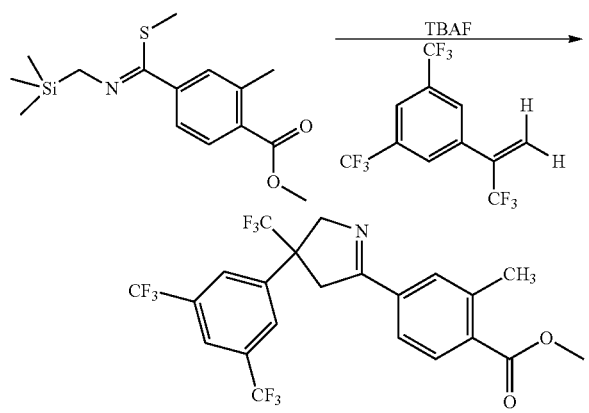

To a solution of 2-methyl-4-(methylsulfanyl-trimethylsilanylmethylimino]-methyl)-benzoic acid methyl ester (Example I9) (135 mg) and 1,3-bis-trifluoromethyl-5-(1-trifluoromethyl-vinyl)-benzene (see WO 2007125984) (179 mg) in THF (5 ml) was added at 5° C. tetrabutylammonium fluoride (TBAF) (0.11 ml, 1M in THF). The reaction mixture was stirred at ambient temperature for 5 hours. The reaction mixture was filtered over silica and concentrated. The residue was purified by preparative HPLC to give 4-[4-(3,5-bis-trifluoromethyl-phenyl)-4-trifluoromethyl-3,4-dihydro-2H-pyrrol-2-yl]-2-methyl-benzoic acid methyl ester (124 mg). ¹H-NMR (400 MHz, CDCl₃): 8.60-7.70 (m, 6H), 5.03 (d, 1H), 4.52 (d, 1H), 3.98-3.90 (m, 4H), 3.55-3.40 (m, 1H), 2.68 (s, 3H) ppm.

2-Methyl-4-[4-(3,4,5-trichloro-phenyl)-4-trifluoromethyl-4,5-dihydro-3H-pyrrol-2-yl]-benzoic acid methyl ester was obtained using a similar procedure. ¹H-NMR (400 MHz, CDCl₃): 8.0-7.42 (m, 5H), 4.90 (d, 1H), 4.45 (d, 1H), 3.93 (s, 3H), 3.80 (d, 1H), 3.45 (d, 1H), 2.65 (s, 3H) ppm.

Example I11

Preparation of 4-[4-(3,5-Bis-trifluoromethyl-phenyl)-4-trifluoromethyl-4,5-dihydro-3H-pyrrol-2-yl]-2-methyl-benzoic acid

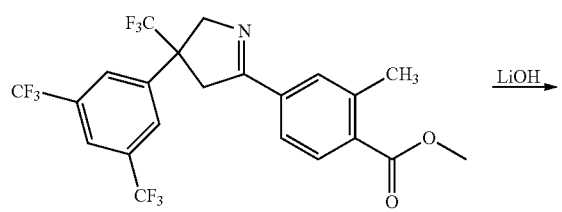

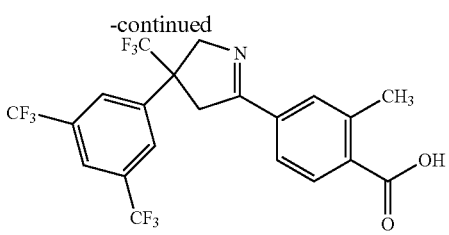

To a solution of 2-methyl-4-(methylsulfanyl-trimethylsilanylmethylimino]-methyl)-benzoic acid methyl ester (Example I10) (115 mg) in THF (4 ml) and water (2 ml) was added Lithium hydroxide monohydrate (24 mg). The reaction mixture was stirred at 50° C. for 16 hours. The reaction mixture was cooled to ambient temperature and diluted with water, acidified by addition of aqueous hydrochloric acid (1M) and extracted twice with ethyl acetate. The combined organic phases were washed with brine, dried over sodium sulfate and concentrated to give 4-[4-(3,5-Bis-trifluoromethyl-phenyl)-4-trifluoromethyl-4,5-dihydro-3H-pyrrol-2-yl]-2-methyl-benzoic acid (109 mg). ¹H-NMR (400 MHz, CDCl₃): 8.15-7.72 (m, 6H), 5.05 (d, 1H), 4.55 (d, 1H), 3.95 (d, 1H), 3.55 (d, 1H), 2.70 (s, 3H) ppm.

2-Methyl-4-[4-(3,4,5-trichloro-phenyl)-4-trifluoromethyl-4,5-dihydro-3H-pyrrol-2-yl]-benzoic acid was obtained using a similar procedure. ¹H-NMR (400 MHz, CDCl₃): 7.95-7.55 (m, 5H), 4.76 (d, 1H), 4.30 (d, 1H), 3.65 (d, 1H), 3.30 (d, 1H), 2.55 (s, 3H) ppm.

Example I12

Preparation of 4-Bromo-3-chloro-N-trimethylsilanylmethyl-benzamide

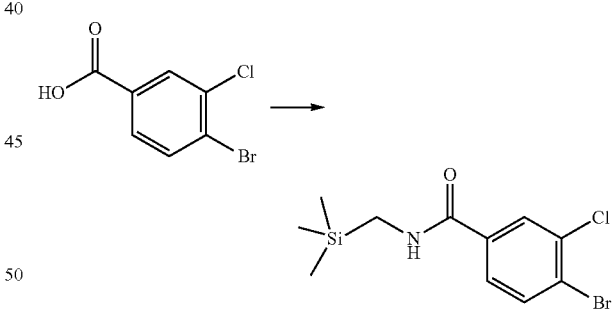

To a solution of 4-bromo-3-chloro-benzoic acid (commercially available) (5.0 g) in dichloromethane (30 ml) was added N-(-3-dimethylaminopropyl)-N'-ethylcarbodiimid hydrochloride (5.29 g), N,N-dimethylaminopyridine (1.19 g) and trimethylsilylmethylamine (2.85 ml). The reaction mixture was stirred at ambient temperature for 5 hours. Water and dichloromethane was added to the reaction mixture. The phases were separated and the organic phase was washed with brine, dried over sodium sulfate and filtered through silica gel. The reaction mixture was concentrated to give 4-bromo-3-chloro-N-trimethylsilanylmethyl-benzamide (4.87 g). 1H-NMR (400 MHz, CDCl₃): 7.68 (d, 1H), 7.55 (s, 1H), 7.33 (d, 1H), 5.85 (s, 1H), 2.84 (d, 2H), 0.00 (s, 9H) ppm.

Example I13

Preparation of 4-Bromo-3-chloro-N-trimethylsilanylmethylthiobenzamide

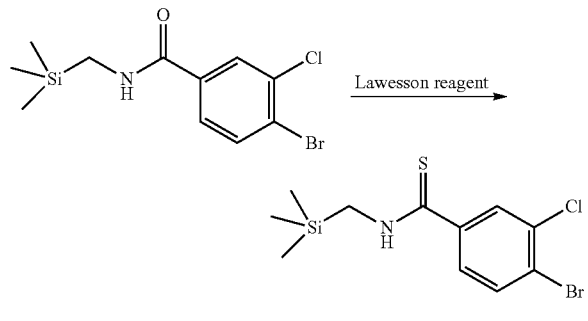

To a solution of 4-bromo-3-chloro-N-trimethylsilanylmethyl-benzamide (Example I12) (4.6 g) in toluene (150 ml) was added 2,4-bis(4-methoxyphenyl)-1,3,2,4-dithiadiphosphetane 2,4-disulfide (Lawesson reagent) (5.8 g). The reaction mixture was stirred at ambient temperature for 30 minutes and then at 110° C. for 1.5 hours. The reaction mixture was concentrated and the residue purified by chromatography on silica gel (eluent: ethyl acetate/heptanes 1:5) to give 4-bromo-3-chloro-N-trimethylsilanylmethylthiobenzamide (4.64 g). 1H-NMR (400 MHz, CDCl$_3$): 1H-NMR (400 MHz, CDCl$_3$): 7.60 (d, 1H), 7.45 (s, 1H), 7.30 (s, 1H), 7.25 (d, 1H), 3.33 (d, 2H), 0.00 (s, 9H) ppm.

Example I14

Preparation of 4-Bromo-3-chloro-N-trimethylsilanylmethyl-thiobenzimidic acid methyl ester

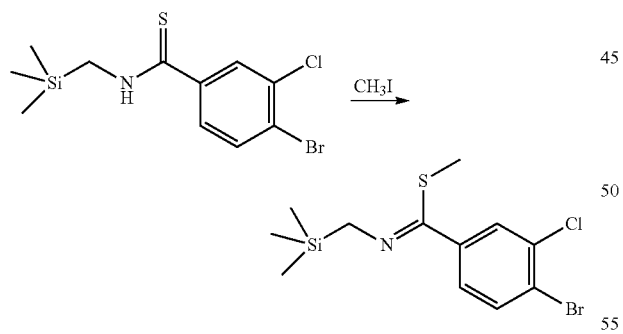

To a solution of 4-bromo-3-chloro-N-trimethylsilanylmethylthiobenzamide (Example I13) (4.43 g) in butanone (80 ml) was added potassium carbonate (2.73 g) and methyl iodide (1.02 ml). The reaction mixture was stirred at ambient temperature for 20 hours. The reaction mixture was concentrated and the residue purified by chromatography on silica gel (eluent: ethyl acetate/heptanes 1:5) to give of 4-bromo-3-chloro-N-trimethylsilanylmethyl-thiobenzimidic acid methyl ester (2.56 g). 1H-NMR (400 MHz, CDCl$_3$): 7.55-7.15 (m, 3H), 3.55 (s, 2H), 1.98 (s, 3H), 0.00 (s, 9H) ppm.

Example I15

Preparation of 5-(4-Bromo-3-chloro-phenyl)-3-(3,5-dichloro-phenyl)-3-methyl-3,4-dihydro-2H-pyrrole

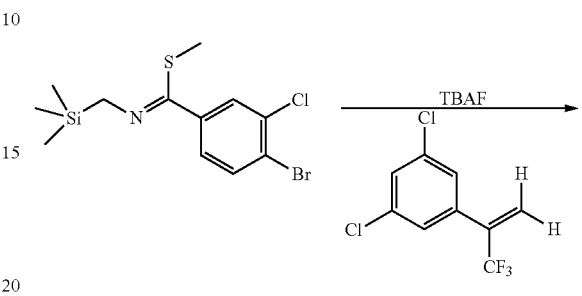

To a solution of 4-bromo-3-chloro-N-trimethylsilanylmethyl-thiobenzimidic acid methyl ester (Example I14) (1.83 g) and 1,3-dichloro-5-(1-trifluoromethyl-vinyl)-benzene (see WO 2007125984) (1.38 g) in THF (25 ml) was added at −5° C. tetrabutylammonium fluoride trihydrate (TBAF) (0.41 g) dissolved in THF (15 ml). The reaction mixture was stirred at ambient temperature for 16 hours. The reaction mixture concentrated and the residue was purified by chromatography on silica gel (eluent: ethyl acetate/heptanes 1:6) to give 5-(4-bromo-3-chloro-phenyl)-3-(3,5-dichloro-phenyl)-3-methyl-3,4-dihydro-2H-pyrrole (2.50 g). $^1$H-NMR (400 MHz, CDCl$_3$): 7.95-7.25 (m, 6H), 4.88 (d, 1H), 4.42 (d, 1H), 3.75 (d, 1H), 3.40 (d, 1H) ppm.

Example I16

Preparation of 2-Chloro-4-[4-(3,5-dichloro-phenyl)-4-trifluoromethyl-4,5-dihydro-3H-pyrrol-2-yl]-benzoic acid butyl ester

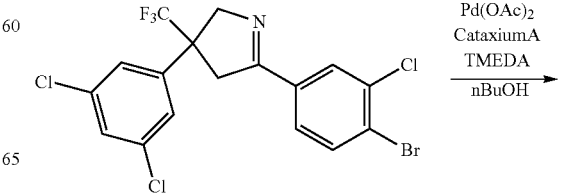

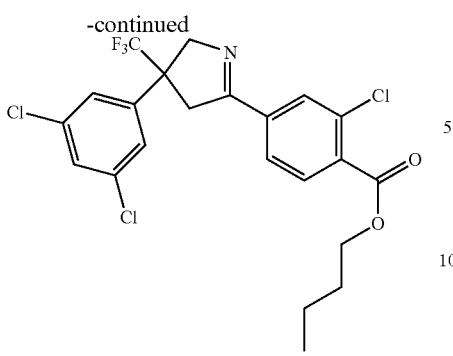

Catraxium A (68 mg) and palladium acetate (13 mg) were dissolved in butanol (30 ml) under an argon atmosphere. Tetramethylene diamine (0.29 ml) and 5-(4-bromo-3-chloro-phenyl)-3-(3,5-dichloro-phenyl)-3-methyl-3,4-dihydro-2H-pyrrole (1.11 g) were added at ambient temperature. The reaction mixture was stirred in a pressure reactor in an atmosphere of carbon monoxide (6 bar) at 115° C. for 16 hours. The reaction mixture was cooled to ambient temperature, filtered and ethyl acetate (250 ml) was added. The mixture was washed with water (50 ml), brine (50 ml), dried over anhydrous sodium sulphate, filtered over a small layer of silica and concentrated. The residue was purified by chromatography on silica gel (eluent: ethyl acetate/heptanes 1:4) to give 2-chloro-4-[4-(3,5-dichloro-phenyl)-4-trifluoromethyl-4,5-dihydro-3H-pyrrol-2-yl]-benzoic acid butyl ester (0.49 g). $^1$H-NMR (400 MHz, CDCl$_3$): 7.95-7.25 (m, 6H), 4.92 (d, 1H), 4.45 (d, 1H), 4.37 (t, 2H), 3.78 (d, 1H), 3.45 (d, 1H), 1.75 (m, 2H), 1.50 (m, 2H), 0.95 (t, 3H) ppm.

Example I17

Preparation of 2-Chloro-4-[4-(3,5-dichloro-phenyl)-4-methyl-4,5-dihydro-3H-pyrrol-2-yl]-benzoic acid

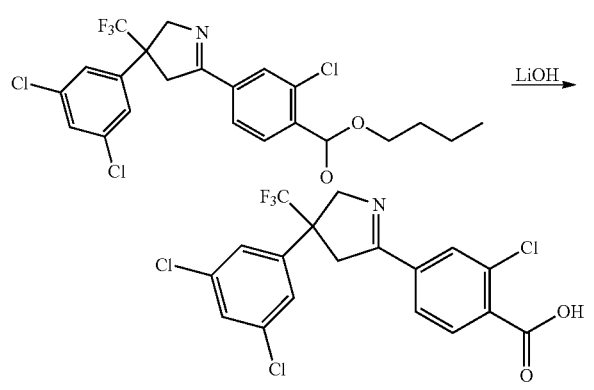

To a solution of 2-chloro-4-[4-(3,5-dichloro-phenyl)-4-trifluoromethyl-4,5-dihydro-3H-pyrrol-2-yl]-benzoic acid butyl ester (Example I16) (0.48 g) in THF (16 ml) and water (8 ml) was added lithium hydroxide monohydrate (103 mg). The reaction mixture was stirred at 50° C. for 20 hours. The reaction mixture was cooled to ambient temperature and diluted with water, acidified by addition of aqueous hydrochloric acid (1M) and extracted twice with ethyl acetate. The combined organic phases were washed with brine, dried over sodium sulfate and concentrated to give 2-chloro-4-[4-(3,5-dichloro-phenyl)-4-trifluoromethyl-4,5-dihydro-3H-pyrrol-2-yl]-benzoic acid (459 mg). $^1$H-NMR (400 MHz, CDCl$_3$): 8.15-7.40 (m, 6H), 4.95 (d, 1H), 4.30 (d, 1H), 3.85 (d, 1H), 3.35 (d, 1H) ppm.

Example I18

Preparation of 2-Methyl-4-{methylsulfanyl-[(Z)-trimethylsilanyl methylimino]methyl}-benzoic acid

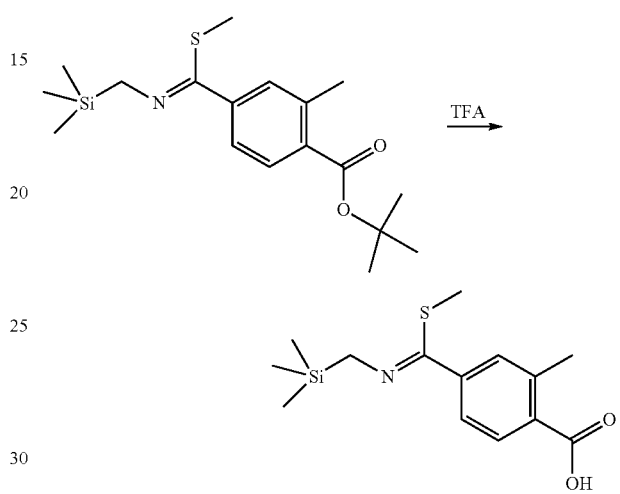

To a solution of 2-methyl-4-{methylsulfanyl-[(E)-trimethylsilanylmethylimino]-methyl}-benzoic acid tert-butyl ester (see Example I9) (118 mg) in dichloromethane (15 ml) was added trifluoroacetic acid (0.22 ml). The reaction mixture was stirred at ambient temperature for 20 hours. Further trifluoroacetic acid (0.11 ml) was added and the mixture was stirred for another 3 hours at ambient temperature. Water was added and the mixture was extracted twice with dichloromethane. The combined organic phases were washed with brine, dried over sodium sulfate and concentrated to give 2-methyl-4-{methylsulfanyl-[(Z)-trimethylsilanyl methylimino]methyl}-benzoic acid which was used without further purification in the subsequent step.

LC-MS (Method A): RT (min): 1.32; [M+H]$^+$:296

Example I19

Preparation of 3-Methyl-4-(thietan-3-ylcarbamoyl)-N-trimethylsilanylmethyl-thiobenzimidic acid methyl ester

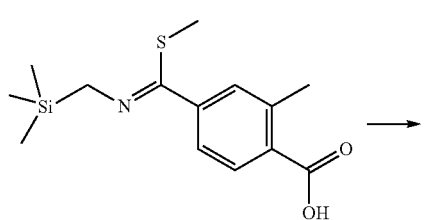

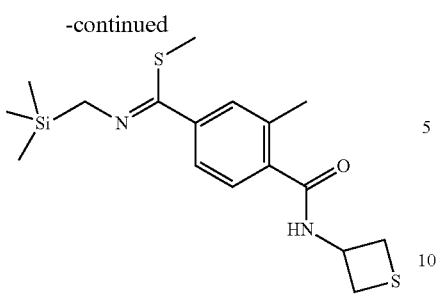

To a solution of 2-methyl-4-{methylsulfanyl-[(Z)-trimethylsilanyl methylimino]methyl}-benzoic acid (Example I18) (107 mg) in dichloromethane (6 ml) was added thietan-3-ylamine (88 mg), Hünigs base (0.248 ml) and 2-bromo-1-ethyl-pyridinium tetrafluoroborate (169 mg). The reaction mixture was stirred at ambient temperature for 2 hours. Water was added and the mixture was extracted twice with dichloromethane. The combined organic phases were washed with brine, dried over sodium sulfate and concentrated. The residue was purified by chromatography on silica gel (eluent: ethyl acetate/heptanes 1:3) to give 3-methyl-4-(thietan-3-ylcarbamoyl)-N-trimethylsilanylmethyl-thiobenzimidic acid methyl ester (16 mg). 1H-NMR (400 MHz, CDCl$_3$): 7.40-7.20 (m, 3H), 6.20 (d, 1H); 5.30 (m, 1H), 3.55 (s, 2H), 3.35 (m, 2H), 3.25 (m, 2H), 2.35 (s, 3H), 1.95 (s, 3H), 0.00 (s, 9H) ppm.

LC-MS (Methode A): RT (min): 1.33; [M+H]$^+$:367

Example I20

Preparation of 4-[4-(3,5-Dichloro-phenyl)-4-trifluoromethyl-4,5-dihydro-3H-pyrrol-2-yl]-2-methyl-N-thietan-3-yl-benzamide

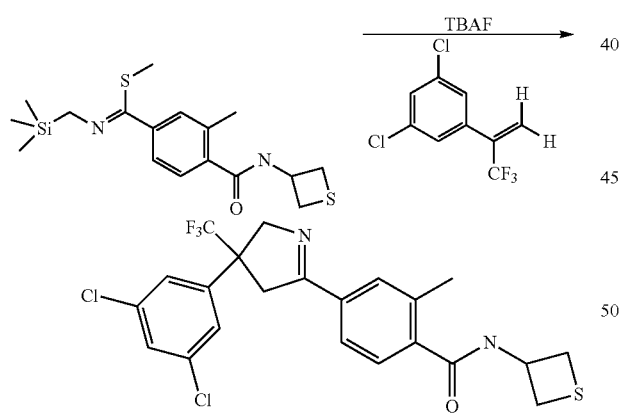

To a solution of 3-methyl-4-(thietan-3-ylcarbamoyl)-N-trimethylsilanylmethyl-thiobenzimidic acid methyl ester (Example I19) (16 mg) and 1,3-dichloro-5-(1-trifluoromethyl-vinyl)-benzene (see WO 2007/125984) (12 mg) in THF (2 ml) was added at −5° C. tetrabutylammonium fluoride trihydrate (TBAF) (0.41 g) dissolved in THF (1.5 ml). The reaction mixture was stirred at ambient temperature for 16 hours. Water was added and the mixture was extracted twice with ethyl acetate. The combined organic phases were washed with brine, dried over sodium sulfate and concentrated. The residue was purified by chromatography on silica gel (eluent: ethyl acetate/heptanes 1:2) to give 4-[4-(3,5-dichloro-phenyl)-4-trifluoromethyl-4,5-dihydro-3H-pyrrol-2-yl]-2-methyl-N-thietan-3-yl-benzamide (20 mg). $^1$H-NMR (400 MHz, CDCl$_3$): 7.75-7.25 (m, 6H), 6.30 (s, 1H), 5.45 (m, 1H), 4.90 (d, 1H), 4.45 (d, 1H), 3.82 (d, 1H), 3.55-3.38 (m, 5H), 2.48 (s, 3H) ppm.

Example I21

Preparation of 4-[3-(3,5-Dichloro-phenyl)-4,4,4-trifluoro-3-nitromethyl-butyryl]-2-methyl-N-thietan-3-yl-benzamide To a solution of 4-[(Z)-3-(3,5-dichloro-phenyl)-4,4,4-trifluoro-but-2-enoyl]-2-methyl-N-thietan-3-yl-benzamide (general preparation described in WO 2009/080250) (100 mg) in DMF (1 ml) nitromethane (0.011 ml) and 1M sodium hydroxide (0.211 ml) was added at ambient temperature. The reaction mixture was stirred at ambient temperature for 1 hour. Water was added and the mixture was extracted twice with ethyl acetate. The combined organic phases were washed with brine, dried over sodium sulfate and concentrated. The residue was purified by prep. HPLC to give 4-[3-(3,5-dichloro-phenyl)-4,4,4-trifluoro-3-nitromethyl-butyryl]-2-methyl-N-thietan-3-yl-benzamide (78 mg). $^1$H-NMR (400 MHz, CDCl$_3$): 7.85-7.20 (m, 6H), 6.25 (d, 1H), 5.62 (d, 1H), 5.45 (m, 2H), 4.15 (d, 1H), 4.00 (d, 1H), 3.58-3.38 (m, 4H), 2.55 (s, 3H) ppm.

Example I22

Preparation of 4-[4-(3,5-Dichloro-phenyl)-4-trifluoromethyl-4,5-dihydro-3H-pyrrol-2-yl]-2-methyl-N-thietan-3-yl-benzamide

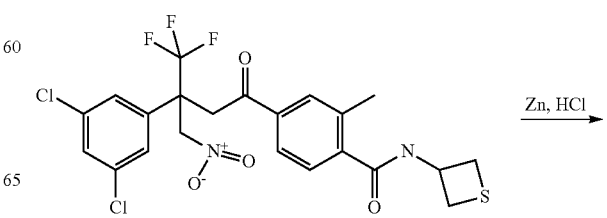

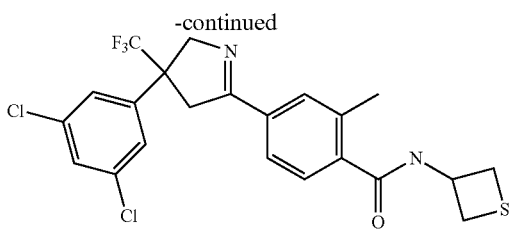

To a solution of 4-[3-(3,5-dichloro-phenyl)-4,4,4-trifluoro-3-nitromethyl-butyryl]-2-methyl-N-thietan-3-yl-benzamide (Example I21) (78 mg) in DMF (1.5 ml) zinc powder (48 mg) was added at ambient temperature. The reaction mixture was heated to 80° C. and concentrated hydrochloric acid (0.3 ml) was added drop-wise. The reaction mixture was stirred at 80° C. for 4 hours. Water was added and the mixture was extracted twice with ethyl acetate. The combined organic phases were washed with brine, dried over sodium sulfate and concentrated. The residue was purified by prep. HPLC to give 4-[4-(3,5-dichloro-phenyl)-4-trifluoromethyl-4,5-dihydro-3H-pyrrol-2-yl]-2-methyl-N-thietan-3-yl-benzamide (12 mg). $^1$H-NMR (400 MHz, CDCl$_3$): 7.75-7.25 (m, 6H), 6.35 (s, 1H), 5.45 (m, 1H), 4.90 (d, 1H), 4.45 (d, 1H), 3.82 (d, 1H), 3.55-3.38 (m, 5H), 2.48 (s, 3H) ppm.

Example P1

Method for Preparing the Compounds of the Invention from a Carboxylic Acid

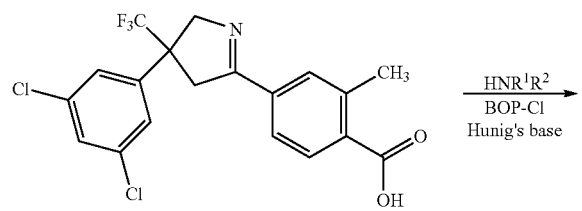

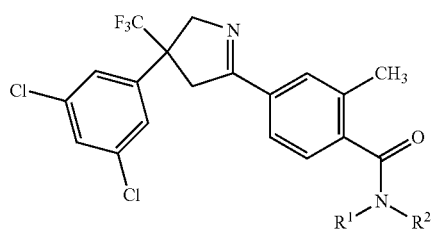

To a solution of the appropriate carboxylic acid (30 μmol), for example 4-[4-(3,5-dichloro-phenyl)-4-trifluoromethyl-4,5-dihydro-3H-pyrrol-2-yl]-2-methyl-benzoic acid (Example I6) in the case of Compound No. A1 of Table A, in dimethylacetamide (0.4 ml) was added successively a solution of an amine of formula HNR$^1$R$^2$ (36 μmol), for example 1,1-dioxo-thietan-3-ylamine (preparation described in, for example, WO 2007/080131) in the case of Compound No. A1 of Table A, in dimethylacetamide (0.145 ml), diisopropylethylamine (Hunig's Base) (0.02 ml, 100 μmol), and a solution of bis(2-oxo-3-oxazolidinyl)phosphonic chloride ("BOP-Cl") (15.3 mg) in dimethylacetamide (0.2 ml). The reaction mixture was stirred at 100° C. for 16 hours. Then the reaction mixture was diluted with acetonitrile (0.6 ml) and a sample was used for LC-MS analysis. The remaining mixture was further diluted with acetonitrile/dimethylformamide (4:1) (0.8 ml) and purified by HPLC. This method was used to prepare a number of compounds (Compound Nos. A1 to A4 of Table A) in parallel. Compounds Nos. A5 to A10, B1 to B4 and C1 to C were obtained using a similar procedure.

TABLE A

Table A provides compounds of formula (Ia) where G is oxygen, R$^3$ is trifluoromethyl, R$^4$ is 3,5-dichloro-phenyl-, R$^5$ is methyl, and R$^1$ and R$^2$ have the values listed in the table below.

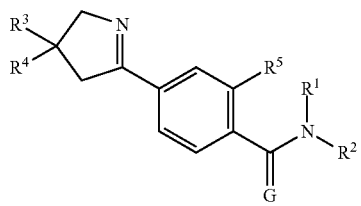

(Ia)

| Compound No. | R$^1$ | R$^2$ | RT (min) | [M + H]$^+$ | LC-MS method |
|---|---|---|---|---|---|
| A1 | H | 1,1-dioxo-thietan-3-yl | 3.04 | 519.0 | C |
| A2 | H | 3-methyl-thietan-3-yl | 3.59 | 501.0 | C |
| A3 | H | 1-oxo-thietan-3-yl- | 2.82 | 503.0 | C |
| A4 | H | thietan-3-yl- | 3.40 | 487.0 | C |
| A5 | H | 1-oxo-cyclobutan-3-yl | 1.97 | 483.0 | A |
| A6 | H | cyclobutanone O-methyl-oxime-3-yl | 2.04 | 512.0 | A |
| A7 | H | cyclobutanone O-benzyl-oxime-3-yl | 2.21 | 588.0 | A |
| A8 | H | thietan-2-yl-methyl- | 2.04 | 501.0 | A |

TABLE A-continued

Table A provides compounds of formula (Ia) where G is oxygen, $R^3$ is trifluoromethyl, $R^4$ is 3,5-dichloro-phenyl-, $R^5$ is methyl, and $R^1$ and $R^2$ have the values listed in the table below.

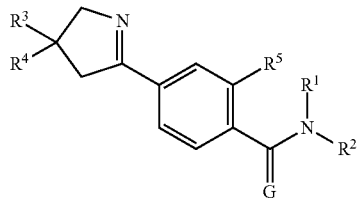

(Ia)

| Compound No. | $R^1$ | $R^2$ | RT (min) | $[M + H]^+$ | LC-MS method |
|---|---|---|---|---|---|
| A9 | H | 1-oxo-thietan-2-yl-methyl- | 1.87 | 517.0 | A |
| A10 | H | 1,1-dioxo-thietan-2-yl-methyl- | 1.90 | 533 | A |

TABLE B

Table B provides compounds of formula (Ia) where G is oxygen, $R^1$ is Hydrogen, $R^5$ is methyl, $R^3$ is trifluoromethyl, and $R^2$ and $R^4$ have the values listed in the table below.

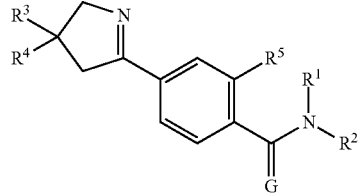

(Ia)

| Compound No. | $R^2$ | $R^4$ | RT (min) | $[M + H]^+$ | LC-MS method |
|---|---|---|---|---|---|
| B1 | thietan-3-yl- | 3,5-Bis trifluoromethyl-phenyl- | 2.12 | 555.0 | A |
| B2 | 1,1-dioxo-thietan-3-yl- | 3,5-Bis trifluoromethyl-phenyl- | 2.00 | 587.0 | A |
| B3 | thietan-3-yl- | 3,4,5-Trichloro-phenyl- | 2.16 | 523.0 | A |
| B4 | 1,1-dioxo-thietan-3-yl- | 3,4,5-Trichloro-phenyl- | 2.03 | 555.0 | A |
| B5 | 1-oxo-thietan-3-yl- | 3,4,5-Trichloro-phenyl- | 1.94 | 539.0 | A |
| B6 | 1-oxo-thietan-3-yl- | 3,5-Bis trifluoromethyl-phenyl- | 1.91 | 571.0 | A |

TABLE C

Table C provides compounds of formula (Ia) where G is oxygen, $R^1$ is Hydrogen, $R^4$ is 3,5-dichloro-phenyl-, and $R^2$, $R^3$ and $R^5$ have the values listed in the table below.

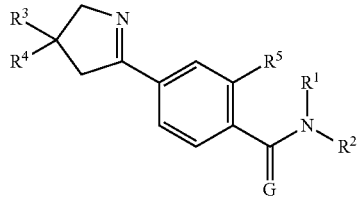

(Ia)

| Compound No. | $R^2$ | $R^3$ | $R^5$ | RT (min) | $[M + H]^+$ | LC-MS method |
|---|---|---|---|---|---|---|
| C1 | thietan-3-yl- | $CF_3$— | Cl— | 2.06 | 509.0 | A |
| C2 | 1,1-dioxo-thietan-3-yl- | $CF_3$— | Cl— | 1.97 | 541.0 | A |
| C3 | 1-oxo-thietan-3-yl- | $CF_3$— | Cl— | 1.88 | 525.0 | A |

TABLE D

Table D provides compounds of formula (Ib) where G is oxygen, $R^3$ is trifluoromethyl, $R^4$ is 3,5-dichloro-phenyl- and $R^1$ and $R^2$ have the values listed in the table below.

(Ib)

| Compound No. | $R^1$ | $R^2$ | RT (min) | $[M + H]^+$ | LC-MS method |
|---|---|---|---|---|---|
| D1 | H | -thietan-3-yl- | 2.09 | 523.0 | A |
| D2 | H | 1-oxo-thietan-3-yl- | 1.93 | 539.0 | A |
| D3 | H | 1,1-dioxo-thietan-3-yl- | 1.97 | 555.0 | A |

Biological Examples

This Example illustrates the insecticidal and acaricidal properties of compounds of formula (I). The tests were performed as follows:

*Spodoptera littoralis* (Egyptian Cotton Leafworm):

Cotton leaf discs were placed on agar in a 24-well microtiter plate and sprayed with test solutions at an application rate of 200 ppm. After drying, the leaf discs were infested with 5 L1 larvae. The samples were checked for mortality, feeding behavior, and growth regulation 3 days after treatment (DAT).

The following compound gave at least 80% control of *Spodoptera littoralis*: A1, A2, A3, A4, A5, A6, A7, A8, A9, A10, B1, B2, B3, B4, B5, B6, C1, C2, C3, D1, D2, D3

*Heliothis virescens* (Tobacco Budworm):

Eggs (0-24 h old) were placed in 24-well microtiter plate on artificial diet and treated with test solutions at an application rate of 200 ppm (concentration in well 18 ppm) by pipetting.

After an incubation period of 4 days, samples were checked for egg mortality, larval mortality, and growth regulation.

The following compound gave at least 80% control of *Heliothis virescens*: A1, A2, A3, A4, A5, A6, A7, A8, A9, A10, B1, B2, B3, B4, B5, B6, C1, C2, C3, D1, D2, D3.

*Plutella xylostella* (Diamond Back Moth):

24-well microtiter plate (MTP) with artificial diet was treated with test solutions at an application rate of 200 ppm (concentration in well 18 ppm) by pipetting. After drying, the MTP's were infested with L2 larvae (7-12 per well). After an incubation period of 6 days, samples were checked for larval mortality and growth regulation.

The following compound gave at least 80% control of *Plutella xylostella*: A1, A2, A3, A4, A5, A6, A7, A8, A9, A10, B1, B2, B3, B4, B5, B6, C1, C2, C3, D1, D2, D3.

*Diabrotica balteata* (Corn Root Worm):

A 24-well microtiter plate (MTP) with artificial diet was treated with test solutions at an application rate of 200 ppm (concentration in well 18 ppm) by pipetting. After drying, the MTP's were infested with L2 larvae (6-10 per well). After an incubation period of 5 days, samples were checked for larval mortality and growth regulation.

The following compound gave at least 80% control of *Diabrotica balteata*: A1, A2, A3, A4, A5, A6, A7, A8, A9, A10, B1, B2, B3, B4, B5, B6, C1, C2, C3, D1, D2, D3.

*Thrips tabaci* (Onion Thrips):

Sunflower leaf discs were placed on agar in a 24-well microtiter plate and sprayed with test solutions at an application rate of 200 ppm. After drying, the leaf discs were infested with an aphid population of mixed ages. After an incubation period of 7 days, samples were checked for mortality.

The following compounds gave at least 80% control of *Thrips tabaci*: A1, A2, A3, A4, A5, A6, A7, A8, A9, A10, B1, B2, B3, B4, B5, B6, C1, C2, C3, D1, D2, D3.

*Tetranychus urticae* (Two-Spotted Spider Mite):

Bean leaf discs on agar in 24-well microtiter plates were sprayed with test solutions at an application rate of 200 ppm. After drying, the leaf discs are infested with mite populations of mixed ages. 8 days later, discs are checked for egg mortality, larval mortality, and adult mortality.

The following compound gave at least 80% control of *Tetranychus urticae*: A1, A2, A3, A4, A5, A6, A7, A8, A9, A10, B1, B2, B3, B4, B5, B6, C1, C2, C3, D1, D2, D3.

The invention claimed is:

1. A compound of formula (I)

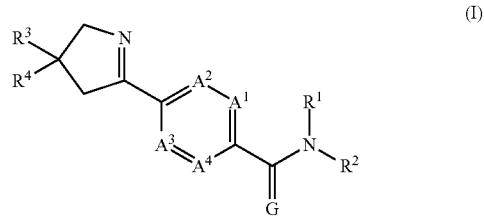

where $A^1$ is C—$R^5$, $A^2$ is C—H, $A^3$ is C—H and $A^4$ is C—H;

G is oxygen;

$R^1$ is hydrogen, methyl, ethyl, methylcarbonyl-, or methoxycarbonyl;

$R^2$ is a group of formula (IIc)

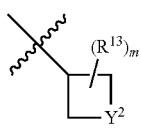

where
$R^{13}$ is $C_1$-$C_8$alkyl,
m is 0, 1, 2, 3, 4, or 5, and
$Y^2$ is S, SO, $SO_2$, S=N—$R^{10}$, SO=N—$R^1$ or C=N—$OR^{10}$;
$R^3$ is chlorodifluoromethyl or trifluoromethyl;
$R^4$ is phenyl substituted by one to three $R^7$;
each $R^5$ is independently halogen, cyano, nitro, $C_1$-$C_8$alkyl, $C_1$-$C_8$haloalkyl, $C_1$-$C_8$alkenyl, $C_1$-$C_8$haloalkenyl, $C_1$-$C_8$alkynyl, $C_1$-$C_8$haloalkynyl, $C_3$-$C_{10}$cycloalkyl, $C_1$-$C_8$alkoxy-, $C_1$-$C_8$haloalkoxy-, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl- or $C_1$-$C_8$haloalkylsulfonyl-, or two $R^5$ on adjacent carbon atoms together form a —CH=CH—CH=CH— bridge;
$R^6$ is hydrogen or $C_1$-$C_8$alkyl;
each $R^7$ is independently bromo, chloro, fluoro, or trifluoromethyl;
each $R^{10}$ is independently hydrogen, cyano, $C_1$-$C_8$alkyl, $C_1$-$C_8$haloalkyl, $C_1$-$C_8$alkyl-carbonyl-, $C_1$-$C_8$haloalkylcarbonyl-, $C_1$-$C_8$alkoxycarbonyl-, $C_1$-$C_8$haloalkoxycarbonyl-, $C_1$-$C_8$alkylsulfonyl-, $C_1$-$C_8$haloalkylsulfonyl-, aryl-$C_1$-$C_4$alkylene- or aryl-$C_1$-$C_4$alkylene- where the aryl moiety is substituted by one to three $R^{12}$, or heteroaryl-$C_1$-$C_4$-$C_4$alkylene- or heteroaryl-$C_1$-$C_4$alkylene- where the heteroaryl moiety is substituted by one to three $R^{12}$;
each $R^{12}$ is independently halogen, cyano, nitro, $C_1$-$C_8$alkyl, $C_1$-$C_8$haloalkyl, $C_1$-$C_8$alkoxy-, $C_1$-$C_8$haloalkoxy- or $C_1$-$C_8$alkoxycarbonyl-;
or a salt or N-oxide thereof.

2. A compound according to claim 1, wherein
$R^1$ is hydrogen, methyl or ethyl;
$R^4$ is 3,5-dibromo-phenyl-, 3,5-dichloro-phenyl-, 3,5-bis-(trifluoromethyl)-phenyl-, 3,4-dichloro-phenyl-, 3,4,5-trichloro-phenyl- or 3-trifluoromethyl-phenyl-;
each $R^5$ is independently bromo, chloro, fluoro, methyl, trifluoromethyl or vinyl, or two $R^5$ on adjacent carbon atoms together form a —CH=CH—CH=CH— bridge; and
each $R^{10}$ is independently methyl or hydrogen.

3. A compound according to claim 1, wherein
$R^1$ is hydrogen;
$R^4$ is 3,5-dibromo-phenyl-, 3,5-dichloro-phenyl-, 3,5-bis-(trifluoromethyl)-phenyl-, 3,4-dichloro-phenyl-, 3,4,5-trichloro-phenyl- or 3-trifluoromethyl-phenyl-;
each $R^5$ is independently bromo, chloro, fluoro, methyl, trifluoromethyl or vinyl, or two $R^5$ on adjacent carbon atoms together form a —CH=CH—CH=CH— bridge; and
each $R^{10}$ is independently methyl or hydrogen.

4. A method of controlling insects, acarines, nematodes or molluscs which comprises applying to a pest, to a locus of a pest, or to a plant susceptible to attack by a pest an insecticidally, acaricidally, nematicidally or molluscicidally effective amount of a compound of formula (I) as defined in claim 1.

5. An insecticidal, acaricidal, nematicidal or molluscicidal composition comprising an insecticidally, acaricidally, nematicidally or molluscicidally effective amount of a compound of formula (I) as defined in claim 1.

6. An insecticidal, acaricidal, nematicidal or molluscicidal composition according to claim 5 comprising an additional compound having biological activity.

7. A method of treatment of insect pests in or on animals, comprising administering an effective amount of a compound as defined in claim 1, or a composition comprising said compound, to an animal.

8. A compound according to claim 1, or a composition comprising said compound, for use in treatment of insect pests in or on animals.

* * * * *